US010358632B2

(12) United States Patent
Jung et al.

(10) Patent No.: US 10,358,632 B2
(45) Date of Patent: Jul. 23, 2019

(54) BACTERIAL CYTOCHROME P450 PROTEIN VARIANT AND METHOD OF REDUCING CONCENTRATION OF FLUORINATED METHANE IN SAMPLE USING THE SAME

(71) Applicant: Samsung Electronics Co., Ltd., Suwon-si, Gyeonggi-do (KR)

(72) Inventors: Yukyung Jung, Hwaseong-si (KR); Dongsik Yang, Hwaseong-si (KR); Jinhwan Park, Suwon-si (KR); Taeyong Kim, Daejeon (KR); Changduk Kang, Gwacheon-si (KR); Anirban Bhaduri, Bangalore (IN); Tadi Venkata Siva Kumar, Bangalore (IN)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 36 days.

(21) Appl. No.: 15/372,327

(22) Filed: Dec. 7, 2016

(65) Prior Publication Data

US 2017/0159030 A1 Jun. 8, 2017

(30) Foreign Application Priority Data

| Dec. 7, 2015 | (KR) | 10-2015-0173293 |
| Apr. 21, 2016 | (KR) | 10-2016-0048960 |
| Jun. 17, 2016 | (KR) | 10-2016-0075831 |
| Aug. 26, 2016 | (KR) | 10-2016-0109543 |
| Aug. 26, 2016 | (KR) | 10-2016-0109544 |

(51) Int. Cl.
*C12N 9/02* (2006.01)
*C12N 9/04* (2006.01)
*C12N 15/70* (2006.01)
*B01D 53/84* (2006.01)
*C02F 3/34* (2006.01)
*B01D 53/85* (2006.01)
*B01D 53/70* (2006.01)
*C02F 101/36* (2006.01)
*C02F 3/02* (2006.01)
*C02F 3/28* (2006.01)

(52) U.S. Cl.
CPC .......... *C12N 9/0077* (2013.01); *B01D 53/84* (2013.01); *B01D 53/85* (2013.01); *C02F 3/342* (2013.01); *C02F 3/348* (2013.01); *C12N 9/0006* (2013.01); *C12N 9/0071* (2013.01); *C12N 15/70* (2013.01); *C12Y 101/01049* (2013.01); *C12Y 114/14001* (2013.01); *C12Y 114/15001* (2013.01); *B01D 53/70* (2013.01); *B01D 2251/95* (2013.01); *B01D 2257/2066* (2013.01); *C02F 3/02* (2013.01); *C02F 3/28* (2013.01); *C02F 2101/36* (2013.01); *Y02W 10/12* (2015.05); *Y02W 10/15* (2015.05)

(58) Field of Classification Search
CPC .......... C12Y 114/14; C12Y 114/14001; C12Y 114/15; C12Y 114/15001
See application file for complete search history.

(56) References Cited

U.S. PATENT DOCUMENTS

| 5,316,940 A | 5/1994 | Georgiou et al. |
| 5,559,278 A | 9/1996 | Mouk et al. |
| 5,637,499 A | 6/1997 | Turick |
| 6,794,168 B1 | 9/2004 | Wong et al. |
| 6,945,925 B2 | 9/2005 | Pooler et al. |
| 8,101,395 B2 | 1/2012 | Davis et al. |
| 8,153,411 B2 | 4/2012 | Short et al. |
| 8,535,910 B2 | 9/2013 | Davis et al. |
| 8,715,988 B2 | 5/2014 | Arnold et al. |
| 2014/0072965 A1 | 3/2014 | Padilla-Crespo et al. |
| 2015/0010945 A1 | 1/2015 | Krajmalnik-Brown et al. |

FOREIGN PATENT DOCUMENTS

| EP | 1433856 A1 | 6/2004 |
| EP | 1500704 A1 | 1/2005 |
| JP | 1994-245761 A | 9/1994 |
| JP | 2005-013872 A | 1/2005 |
| JP | 2008-086850 A | 4/2008 |
| JP | 2010-517579 A | 5/2010 |
| KR | 1997-0707288 B1 | 12/1997 |
| KR | 0392185 B1 | 7/2003 |
| KR | 2004-0064826 B1 | 7/2004 |
| KR | 2005-0028278 A | 3/2005 |
| KR | 2009-0129430 A | 12/2009 |
| WO | WO 98/36080 A1 | 8/1998 |
| WO | WO 2008/016709 A2 | 2/2008 |

OTHER PUBLICATIONS

Castro et al., Biodehalogenation: Reactions of Cytochrome P-450 with Polyhalomethanes, *Biochemistry*, 24(1): 204-210 (1985).
Chen, M.M.Y. (2011). Directed Evolution of Cytochrome P450 for Small Alkane Hydroxylation (Doctor of Philosophy Thesis). California Institute of Technology, Pasadena, California, USA.
Harkey et al., Deflourination of 4-fluorophenol by Cytochrome P450BM3-F87G: Activation by long Chain Fatty Aldehydes, *Biotechnology Letters*, 34 (9):1725-1731 (2012).
Li et al., Reductive Dehalogenation by Cytochrome P450$_{cam}$: Substrate Binding and Catalysis, *Biochemistry*, 32(36): 9355-9361 (1993).
Luke et al., "Theoretical Investigation of the Anaerobic Reduction of Halogenated Alkanes by Cytochrome P-450", *J. Am. Chem. Soc.*, 110 (11): 3396-3400 (1988).
Manchester et al., Enzyme-catalyzed dehalogenation of pentachloroethane: why F87W-cytochrome P450cam is faster than wild type, *Protein Engineering*, 8 (8): 801-807 (1995).

(Continued)

*Primary Examiner* — Karen Cochrane Carlson
(74) *Attorney, Agent, or Firm* — Leydig, Voit & Mayer, Ltd.

(57) ABSTRACT

Provided is a recombinant microorganism including an exogenous gene encoding a bacterial cytochrome P450 protein or a variant thereof, a composition including the recombinant P450 protein or the variant thereof, which is used for removing $CH_nF_{4-n}$ (n is an integer of 0 to 3) in a sample, and a method of reducing a concentration of $CH_nF_{4-n}$ in the sample.

31 Claims, 8 Drawing Sheets

Specification includes a Sequence Listing.

(56) References Cited

OTHER PUBLICATIONS

Wackett et al., "Metabolism of polyhalogenated compounds by a genetically engineered bacterium", *Nature*, 368: 627-628 (1994).
Yasukochi et al., Putative functions of phenylalanine-350 of *Pseudomonas putida* cytochrome P-450$_{cam}$, *Biochimica et Biophysica Acta*, 1204(1):84-90 (1994).
Csaki et al., Genes involved in the copper-dependent regulation of soluble methane monooxygenase of *Methyloccus capsulatus* (Bath): cloning, sequencing and mutational analysis, *Microbiology*, 149:1785-1795 (2003).
Janssen et al., Cloning of 1,2-Dichloroethene Degradation Genes of *Xanthobacter autrophicus* GJ10 and Expression and Sequencing of the dhlA Gene, *Journal of Bacteriology*, 171(12): 6791-6799 (1989).
Liu et al., Reaction Mechanism of Fluoroacetate Dehalogenase from *Moraxella* sp. B, *The Journal of Biological Chemistry*, 273(47):30897-30902 (1998).
Peterson et al., Putidaredoxin Reductase and Putidaredoxin, *The Journal of Biological Chemistry*, 265(11): 6068-6073 (1990).
Van Der Ploeg et al., Characterization of the Haloacid Dehalogenase from *Xanthobacter autrophicus* GJ10 and Sequencing of the dhlB Gene, *Journal of Bacteriology*, 173(24): 7925-7933 (1991).
European Patent Office, Extended European Search Report for Application No. 16169537.4, dated Feb. 13, 2017, 14 pp.
European Patent Office, Extended European Search Report for Application No. 16202662.9, dated Mar. 22, 2017, 11 pp.
Hyman et al., "Oxidation of Methyl Fluoride and Dimethyl Ether by Ammonia Monooxygenase in Nitrosomonas europaea", *Applied and Environmental Microbiology*, 60(8): 3033-3035 (1994).
European Patent Office, Office Action in European Application No. 16169537.4 (dated Jul. 26, 2018).
Beauvais et al., "Reactions of the diiron(IV) intermediate Q in soluble methane monooxygenase with fluoromethanes", *Biochemical and Biophysical Research Communications*, 338:262-266 (2005).
Bernardes et al., "Energetics of C—F C—Cl, C—Br, and C—I Bonds in 2-Haloethanols. Enthalpies of Formation of XCH$_2$CH$_2$OH (X=F, Cl, Br, I) Compounds and of the 2-Hydroxyethyl Radical", *J. Phys. Chem. A.*, 111(9): 1713-1720 (2007).
Borodina et al., "Mutagenesis of the "Leucine Gate" to explore the basis of catalytic versatility in soluble methane monooxygenase", *Applied and Environmetnal Microbiology*, 73 (20): 6460-6467 (2007).
Brühlmann et al., "Engineering cytochrome P450 BM3 of *Bacillus megaterium* for terminal oxidation of palmitic acid", *Journal of Biotechnology*, 184:17-26 (2014).
Harford-Cross et al., "Protein engineering of cytochrome P450$_{cam}$ (CYP101) for the oxidation of polycyclic aromatic hydrocarbons", *Protein Engineering*, 13(2): 121-128 (2000).
Jahng et al., "Trichloroethylene and Chloroform Degradation by a Recombinant Pseudomonad Expressing Soluble Methane Monooxygenase from *Methylosinus trichosporium* OB3b," *Applied and Environmental Microbiology*, 60(7): 2473-2482 (1994).
Keuning et al., "Purification and Characterization of Hydrolytic Haloalkane Dehalogenase from *Xanthobacter autrophicus* GJ10", *Journal of Bacteriology*, 163(2): 635-639 (1985).
Kmunicek et al., "Comparative Binding Energy Analysis of the Substrate Specificity of Haloalkane Dehalogenase from *Xanthobacter autotrophicus* GJ10", *Biochemistry*, 40: 8905-8917 (2001).
Kurihara et al., "Purification, characterization, and gene cloning of a novel fluoroacetate dehalogenase from *Burkholderia* sp. FA1", *Journal of Molecular Catalysis B. Enzymatic*, 23: 347-355 (2003).
Penny et al., "Microbial degradation of tetrachloromethane: mechanisms and perspectives for bioremediation", *FEMS Microbiol Eccl*, 74: 257-275 (2010).
Schanstra et al., "Specificity and Kinetics of Haloalkane Dehalogenase", *The Journal of Biological Chemistry*, 271(25): 14747-14753 (1996).
Smith et al., "Improved System for Protein Engineering of the Hydroxylase Component of Soluble Methane Monooxygenase", *Applied and Environmental Microbiology*, 68(11): 5265-5273 (2002).
West et al., "Functional expression *Escherichia coli* of proteins B and C from soluble methane monooxygenase of *Methylococcus capsulantus* (Bath)", *Journal of General Microbiology*, 138(7):1301-1307 (1992).

BACTERIAL CYTOCHROME P450 PROTEIN VARIANT AND METHOD OF REDUCING CONCENTRATION OF FLUORINATED METHANE IN SAMPLE USING THE SAME

CROSS-REFERENCE TO RELATED APPLICATIONS

This application claims the benefit of Korean Patent Application No. 10-2015-0173293, filed on Dec. 7, 2015, Korean Patent Application No. 10-2016-0048960, filed on Apr. 21, 2016, Korean Patent Application No. 10-2016-0075831, filed on Jun. 17, 2016, Korean Patent Application No. 10-2016-0109543, filed on Aug. 26, 2016, and Korean Patent Application No. 10-2016-0109544, filed on Aug. 26, 2016, in the Korean Intellectual Property Office, the entire disclosures of which are hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 74,978 Byte ASCII (Text) file named "727150_ST25.TXT," created on Dec. 6, 2016.

BACKGROUND

1. Field

The present disclosure relates to a recombinant microorganism including an exogenous gene encoding a bacterial cytochrome P450 protein, a composition including the recombinant P450 protein, which is used for removing fluorinated methane represented by $CH_nF_{4-n}$ (n is an integer of 0 to 3) in a sample, and a method of reducing a concentration of $CH_nF_{4-n}$ in the sample.

2. Description of the Related Art

The emissions of greenhouse gases which have accelerated global warming are one of the serious environmental problems, and regulations to reduce and prevent the emissions of greenhouse gases have been tightened. Among the greenhouse gases, fluorinated gases (F-gas) such as perfluorocarbons (PFCs), hydrofluorocarbons (HFCs), and sulfur hexafluoride ($SF_6$) show low absolute emission, but have a long half-life and a very high global warming potential, resulting in significant adverse environmental impacts. The amount of F-gas emitted from semiconductor and electronics industries, which are major causes of F-gas emission, has exceeded the assigned amount of greenhouse gas emissions and continues to increase. Therefore, costs required for degradation of greenhouse gases and greenhouse gas emission allowances are increasing every year.

A pyrolysis or catalytic thermal oxidation process has been generally used in the decomposition of F-gas. However, this process has disadvantages of limited decomposition rate, emission of secondary pollutants, high cost, etc. To help solve this problem, biological decomposition of F-gas using a microbial biocatalyst has been adopted. Nevertheless, there remains a need for new methods and compositions for removing fluorinated methanes.

SUMMARY

An aspect provides a recombinant microorganism including an exogenous gene encoding a bacterial cytochrome P450 protein or a variant thereof.

Another aspect provides a composition including the recombinant P450 protein or the variant thereof, which is used for removing fluorinated methane represented by $CH_nF_{4-n}$ (n is an integer of 0 to 3) in a sample.

Still another aspect provides a method of reducing a concentration of $CH_nF_{4-n}$ in a sample, the method including contacting the recombinant P450 protein or the variant thereof with the sample containing fluorinated methane represented by $CH_nF_{4-n}$ (n is an integer of 0 to 3) to reduce the concentration of fluorinated methane in the sample.

Still another aspect provides the variant of bacterial cytochrome P450 protein and a polynucleotide encoding the same.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
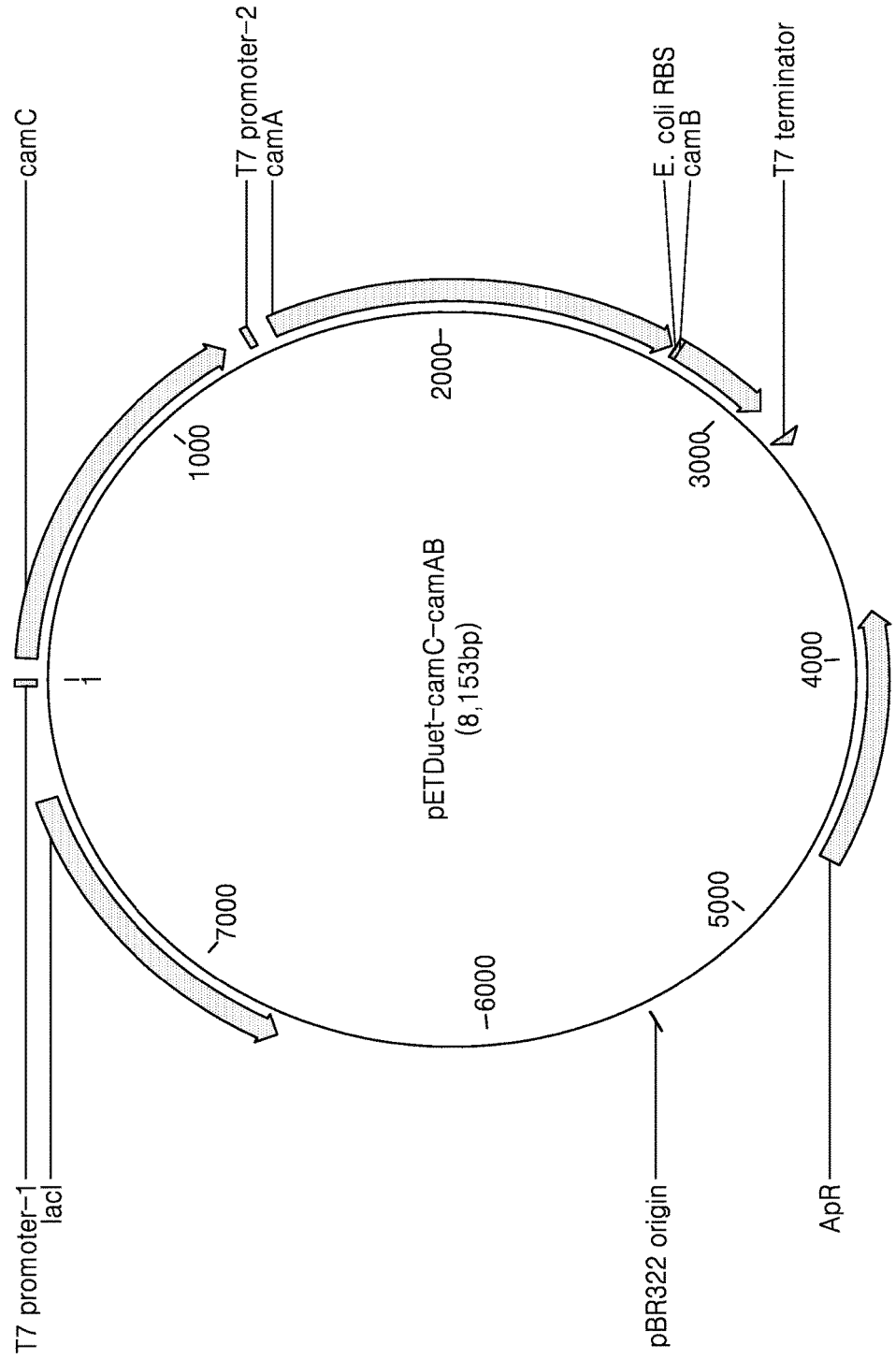
FIG. 1 shows a vector map of a pETDuet-camC-camAB vector.

An aspect provides a recombinant microorganism including an exogenous gene encoding a bacterial cytochrome P450 protein or a variant thereof.

Cytochromes P450 (CYPs) belong to the superfamily of proteins containing a heme cofactor, and therefore, are hemoproteins. Cytochromes P450 use a variety of small and large molecules as substrates in enzymatic reactions. They are, in general, terminal oxidase enzymes in electron transfer chains, broadly categorized as P450-containing systems.

Bacterial cytochromes P450 are often soluble enzymes and are involved in diverse metabolic processes. Some bacteria such *E. coli* have no cytochrome P450. Cytochrome P450 (CYP101) derived from *P. putida* is part of a camphor-hydroxylating catalytic cycle consisting of two electron transfer steps from putidaredoxin, which is a 2Fe-2S cluster-containing protein cofactor.

Cytochrome P450 BM3 (CYP102) derived from *B. megaterium* catalyzes the NADPH-dependent hydroxylation of several long-chain fatty acids at the ω-1 through ω-3 positions. Cytochrome P450 BM3 constitutes a natural fusion protein between the CYP domain and an electron donating cofactor.

With regard to the recombinant microorganism, the cytochrome P450 protein may belong to EC 1.14.15.1 or EC 1.14.14.1. The cytochrome P450 protein may be P450Cam or P450$_{BM3}$.

P450Cam may be derived from *Pseudomonas putida* PpG786. P450$_{BM3}$ may be derived from *Bacillus megaterium* (ATCC 14581). The cytochrome P450$_{CAM}$ protein may be a complex of CamA, CamB, and CamC, which constitutes the bacterial CYP101 system. CamA may be FAD-containing reductase. CamA may be NADH or NADPH-dependent. The CamA may belong to EC 1.18.1.5. CamB may be [2Fe2S]-type ferredoxin. CamC, also called P450Cam(CYP101), may include cytochrome P450 and may belong to EC 1.14.15.1. CamA, CamB, and CamC may have amino acid sequences of SEQ ID NOS: 2, 4, and 6, respectively. Genes encoding CamA, CamB, and CamC may have nucleotide sequences of SEQ ID NOS: 1, 3, and 5, respectively.

The P450Cam variant may have an amino acid alteration at an amino acid residue corresponding to position F351 of an amino acid sequence of SEQ ID NO: 6, and may have an activity belonging to EC 1.14.15.1. The amino acid alteration may be replacement of the amino acid residue corresponding to position F351 with a different amino acid, for example, any of the 19 natural amino acids. For instance, the variant may have replacement (substitution) of the amino acid residue corresponding to the position F351 of SEQ ID NO: 6 with Y, T, N, Q, H, or D (e.g., a F351Y, F351T, F351N, F351Q, F351H, or F351D variant). EC 1.14.15.1 may represent an enzyme that catalyzes the reaction of (+)-camphor+reduced putidaredoxin+O$_2$ ⇔ (+)-exo-5-hydroxycamphor+oxidized putidaredoxin+H$_2$O.

A gene encoding the P450CAM variant may be a gene encoding the F351Y, F351T, F351N, F351Q, F351H, or F351D variant in P450CAM having the amino acid sequence of SEQ ID NO: 6. The gene may have a nucleotide sequence of SEQ ID NO: 51, 52, 53, 54, 55, or 56, or corresponding sequence by virtue of the degeneracy of the genetic code (e.g., a codon-optimized sequence). The microorganism may further include a gene encoding CamA and a gene encoding CamB.

P450$_{BM3}$ may be a polypeptide having an amino acid sequence of SEQ ID NO: 8. A gene encoding P450$_{BM3}$ may have a nucleotide sequence of SEQ ID NO: 7. The variant may have an amino acid alteration at an amino acid residue corresponding to the position N320 of the amino acid sequence of SEQ ID NO: 8, and may have an activity belonging to EC 1.14.14.1. The amino acid alteration may be replacement (substitution) of the amino acid residue corresponding to the position N320 with a different amino acid, for example, any of the 19 natural amino acids. The variant may have replacement of the amino acid residue corresponding to the position N320 of SEQ ID NO: 8 with W, F, G, P, S, or E (e.g., a N320W, N320F, N320G, N320P, N320S, or N320E variant). A gene encoding the P450BM3 variant may be a gene encoding the variant having a N320W, N320F, N320G, N320P, N320S, or N320E substation in P450BM3 having the amino acid sequence of SEQ ID NO: 8. The gene may have a nucleotide sequence of SEQ ID NO: 45, 46, 47, 48, 49, or 50, or corresponding sequence by virtue of the degeneracy of the genetic code (e.g., a codon-optimized sequence).

"EC 1.14.14.1" may catalyze the following reaction: RH+reduced NADPH - - - hemoprotein reductase+ O$_2$=ROH+oxidized NADPH - - - hemoprotein reductase+ H$_2$O.

As used herein, the term "corresponding" refers to the amino acid position of a protein of interest that aligns with the mentioned position (e.g., position F351 of SEQ ID NO: 6 or position N320 of SEQ ID NO: 8) of a reference protein when amino acid sequences of the protein of interest and the reference protein are aligned using an art-acceptable protein alignment program, including the NCBI BLAST pairwise alignment or the well known Lipman-Pearson Protein Alignment program, with the following parameters: Ktuple=2, Gap Penalty=4, and Gap length penalty=12. In this regard, the range included in the "corresponding" sequence may be a range of E-value 0.00001 and H-value 0.001.

Examples of proteins homologs of P450CAM with an amino acid substitution at a position corresponding to position F351 of SEQ ID NO: 6, obtained according to the above alignment conditions, are listed in the following Tables 1, 2, and 3. In Tables 1, 2, and 3, the column labeled "NO." is an arbitrary reference number, and the column labeled "NCBI ID" contains the National Center for Biotechnology Information (NCBI) protein database sequence identification number ("NCBI ID").

Also, examples of homologs of P450BM3 with an amino acid substitution at a position corresponding to position N320 of SEQ ID NO: 8, obtained according to the above alignment conditions, are listed in Table 4. In Table 4, the column labeled "NO." is an arbitrary reference number, and the column labeled "NCBI ID" contains the National Center for Biotechnology Information (NCBI) protein database sequence identification number ("NCBI ID").

Thus, in some embodiments, the P450 variant can comprise SEQ ID NO: 6 with the described substitution at F351 of SEQ ID NO: 6, or can comprise SEQ ID NO: 8 with the described substitution at N320 of SEQ ID NO: 8, or can comprise a different amino acid sequence with a substation at a corresponding amino acid residue, provided it catalyzes the same reaction as the p450 variant comprising SEQ ID NO: 6 or 8 with the indicated substitution. In some embodiments, the p450 variant comprises an amino acid sequence with at least 75, 80, 85, 90, 91, 93, 94, 95, 95, 97, 98, or 99% sequence identity to SEQ ID NO: 6 or SEQ ID NO: 8, including the amino acid alteration at F351 of SEQ ID NO: 6 or N320 of SEQ ID NO: 8. Also contemplated are fragments (e.g., N or C terminal truncations or internal deletions) that retain the recited activity.

TABLE 1

| NO. | NCBI ID |
|---|---|
| 1 | gi\|163930960 |
| 2 | gi\|612182735 |
| 3 | gi\|497125935 |
| 4 | gi\|310942843 |
| 5 | gi\|657832383 |
| 6 | gi\|498088271 |
| 7 | gi\|544829275 |
| 8 | gi\|861974080 |
| 9 | gi\|738620841 |

TABLE 1-continued

| NO. | NCBI ID |
|---|---|
| 10 | gi\|499763441 |
| 11 | gi\|746290673 |
| 12 | gi\|503614840 |
| 13 | gi\|861969570 |
| 14 | gi\|662139213 |
| 15 | gi\|544827262 |
| 16 | gi\|498088269 |
| 17 | gi\|861974085 |
| 18 | gi\|737512009 |
| 19 | gi\|817101596 |
| 20 | gi\|494439068 |
| 21 | gi\|496309894 |
| 22 | gi\|746289514 |
| 23 | gi\|753796069 |
| 24 | gi\|545454562 |
| 25 | gi\|648417306 |
| 26 | gi\|666681698 |
| 27 | gi\|567402060 |
| 28 | gi\|826044703 |
| 29 | gi\|826049125 |
| 30 | gi\|806905723 |
| 31 | gi\|551338874 |
| 32 | gi\|730289226 |
| 33 | gi\|654615031 |
| 34 | gi\|656116930 |
| 35 | gi\|826046029 |
| 36 | gi\|737567226 |
| 37 | gi\|98976439 |
| 38 | gi\|612108073 |
| 39 | gi\|515116019 |
| 40 | gi\|817101463 |
| 41 | gi\|398136480 |
| 42 | gi\|757698965 |
| 43 | gi\|126194726 |
| 44 | gi\|737644672 |
| 45 | gi\|496199226 |
| 46 | gi\|654614522 |
| 47 | gi\|759387698 |
| 48 | gi\|739341634 |
| 49 | gi\|783098869 |
| 50 | gi\|783093808 |
| 51 | gi\|783094059 |
| 52 | gi\|759427060 |
| 53 | gi\|861968800 |
| 54 | gi\|497509581 |
| 55 | gi\|497810537 |
| 56 | gi\|783098865 |
| 57 | gi\|739341585 |
| 58 | gi\|783097592 |
| 59 | gi\|783099978 |
| 60 | gi\|783097681 |
| 61 | gi\|728824802 |
| 62 | gi\|746238551 |
| 63 | gi\|494955160 |
| 64 | gi\|496104589 |
| 65 | gi\|567412687 |
| 66 | gi\|98976470 |
| 67 | gi\|358240604 |
| 68 | gi\|494898237 |
| 69 | gi\|504740033 |
| 70 | gi\|648547795 |
| 71 | gi\|808659667 |
| 72 | gi\|551292036 |
| 73 | gi\|551292470 |
| 74 | gi\|502616812 |
| 75 | gi\|545316934 |
| 76 | gi\|491842667 |
| 77 | gi\|750353906 |
| 78 | gi\|858007594 |
| 79 | gi\|665981585 |
| 80 | gi\|806833869 |
| 81 | gi\|504197805 |
| 82 | gi\|564970689 |
| 83 | gi\|499924508 |
| 84 | gi\|765348796 |
| 85 | gi\|497424876 |
| 86 | gi\|739367531 |
| 87 | gi\|517897868 |
| 88 | gi\|702839727 |
| 89 | gi\|739883834 |
| 90 | gi\|750419370 |

TABLE 2

| NO. | NCBI ID |
|---|---|
| 91 | gi\|494019567 |
| 92 | gi\|498089540 |
| 93 | gi\|826041014 |
| 94 | gi\|566044904 |
| 95 | gi\|566044935 |
| 96 | gi\|501296495 |
| 97 | gi\|517247251 |
| 98 | gi\|516019877 |
| 99 | gi\|288913356 |
| 100 | gi\|512734904 |
| 101 | gi\|783100677 |
| 102 | gi\|764994003 |
| 103 | gi\|517247290 |
| 104 | gi\|652940833 |
| 105 | gi\|169821418 |
| 106 | gi\|835531786 |
| 107 | gi\|551362264 |
| 108 | gi\|764960072 |
| 109 | gi\|759387686 |
| 110 | gi\|737512189 |
| 111 | gi\|820802680 |
| 112 | gi\|646534628 |
| 113 | gi\|820802864 |
| 114 | gi\|334103741 |
| 115 | gi\|826041595 |
| 116 | gi\|746241621 |
| 117 | gi\|764993875 |
| 118 | gi\|748599849 |
| 119 | gi\|764997807 |
| 120 | gi\|662354752 |
| 121 | gi\|783096369 |
| 122 | gi\|530258733 |
| 123 | gi\|657922982 |
| 124 | gi\|654614517 |
| 125 | gi\|739616950 |
| 126 | gi\|783098022 |
| 127 | gi\|806908467 |
| 128 | gi\|21467173 |
| 129 | gi\|401808868 |
| 130 | gi\|514397583 |
| 131 | gi\|749201634 |
| 132 | gi\|528182079 |
| 133 | gi\|647795133 |
| 134 | gi\|651636595 |
| 135 | gi\|661269250 |
| 136 | gi\|695263348 |
| 137 | gi\|696511194 |
| 138 | gi\|493217416 |
| 139 | gi\|493377553 |
| 140 | gi\|563565380 |
| 141 | gi\|665834124 |
| 142 | gi\|665888884 |
| 143 | gi\|665827329 |
| 144 | gi\|751294725 |
| 145 | gi\|827106327 |
| 146 | gi\|639165413 |
| 147 | gi\|652899356 |
| 148 | gi\|652914977 |
| 149 | gi\|652694819 |
| 150 | gi\|496153669 |
| 151 | gi\|518973859 |
| 152 | gi\|808102361 |
| 153 | gi\|664078266 |
| 154 | gi\|663221595 |
| 155 | gi\|663326563 |
| 156 | gi\|493424288 |
| 157 | gi\|502993954 |

TABLE 2-continued

| NO. | NCBI ID |
|---|---|
| 158 | gi|518949456 |
| 159 | gi|750417303 |
| 160 | gi|750543392 |
| 161 | gi|377530614 |
| 162 | gi|377532462 |
| 163 | gi|737965741 |
| 164 | gi|739538229 |
| 165 | gi|739543125 |
| 166 | gi|750407524 |
| 167 | gi|739645497 |
| 168 | gi|493919745 |
| 169 | gi|737792710 |
| 170 | gi|750519055 |
| 171 | gi|521297725 |
| 172 | gi|482632482 |
| 173 | gi|494797766 |
| 174 | gi|493993588 |
| 175 | gi|648280499 |
| 176 | gi|750519223 |
| 177 | gi|498814706 |
| 178 | gi|519015945 |
| 179 | gi|639007804 |
| 180 | gi|518767974 |

TABLE 3

| NO. | NCBI ID |
|---|---|
| 181 | gi|739625293 |
| 182 | gi|820802866 |
| 183 | gi|739651753 |
| 184 | gi|502742128 |
| 185 | gi|515118033 |
| 186 | gi|820802677 |
| 187 | gi|391860290 |
| 188 | gi|737643185 |
| 189 | gi|544823238 |
| 190 | gi|763095543 |
| 191 | gi|739611016 |
| 192 | gi|145322598 |
| 193 | gi|825391797 |
| 194 | gi|759685456 |
| 195 | gi|836723496 |
| 196 | gi|488703345 |
| 197 | gi|763384158 |
| 198 | gi|528059914 |
| 199 | gi|783097229 |
| 200 | gi|494017068 |
| 201 | gi|739663478 |
| 202 | gi|739620206 |
| 203 | gi|746237691 |
| 204 | gi|567412712 |
| 205 | gi|550925359 |
| 206 | gi|746344573 |
| 207 | gi|530255704 |
| 208 | gi|739669024 |
| 209 | gi|654478200 |
| 210 | gi|490753280 |
| 211 | gi|497922631 |
| 212 | gi|740896970 |
| 213 | gi|652908779 |
| 214 | gi|503298839 |
| 215 | gi|740869740 |
| 216 | gi|503612867 |
| 217 | gi|646519758 |
| 218 | gi|494981163 |
| 219 | gi|490214493 |
| 220 | gi|736859678 |
| 221 | gi|739577671 |
| 222 | gi|736886954 |
| 223 | gi|654534319 |
| 224 | gi|549129549 |
| 225 | gi|653383901 |
| 226 | gi|703388673 |
| 227 | gi|653777500 |

TABLE 3-continued

| NO. | NCBI ID |
|---|---|
| 228 | gi|655968891 |
| 229 | gi|655882347 |
| 230 | gi|630947972 |
| 231 | gi|495218410 |
| 232 | gi|768967538 |
| 233 | gi|746229913 |
| 234 | gi|746230981 |
| 235 | gi|746236533 |
| 236 | gi|544823589 |
| 237 | gi|746239269 |
| 238 | gi|490319630 |
| 239 | gi|494981649 |
| 240 | gi|494957004 |
| 241 | gi|763090173 |
| 242 | gi|738613213 |
| 243 | gi|746229737 |
| 244 | gi|754958228 |
| 245 | gi|499912932 |
| 246 | gi|657825087 |
| 247 | gi|655586613 |
| 248 | gi|739190742 |
| 249 | gi|518714103 |
| 250 | gi|503189844 |
| 251 | gi|739186131 |
| 252 | gi|739186149 |
| 253 | gi|516607102 |
| 254 | gi|522116265 |
| 255 | gi|522150263 |
| 256 | gi|703225980 |
| 257 | gi|703223632 |
| 258 | gi|703223663 |
| 259 | gi|494300956 |
| 260 | gi|808659227 |
| 261 | gi|489969104 |
| 262 | gi|806822276 |
| 263 | gi|556618018 |
| 264 | gi|738609029 |
| 265 | gi|403646243 |
| 266 | gi|737785331 |
| 267 | gi|703226655 |
| 268 | gi|602519307 |
| 269 | gi|739367513 |
| 270 | gi|737980497 |
| 271 | gi|737981631 |
| 272 | gi|817101442 |
| 273 | gi|497809551 |
| 274 | gi|545453717 |
| 275 | gi|497809089 |

TABLE 4

| NO. | NCBI ID |
|---|---|
| 1 | gi|515136080 |
| 2 | gi|757757972 |
| 3 | gi|822528663 |
| 4 | gi|544838284 |
| 5 | gi|491696887 |
| 6 | gi|655149838 |
| 7 | gi|512150124 |
| 8 | gi|493729782 |
| 9 | gi|738856821 |
| 10 | gi|655112080 |
| 11 | gi|648634781 |
| 12 | gi|522106669 |
| 13 | gi|504462655 |
| 14 | gi|783152040 |
| 15 | gi|759010788 |
| 16 | gi|545381104 |
| 17 | gi|548617766 |
| 18 | gi|648623486 |
| 19 | gi|738714376 |
| 20 | gi|639453808 |
| 21 | gi|497281073 |
| 22 | gi|494207912 |

TABLE 4-continued

| NO. | NCBI ID |
|---|---|
| 23 | gi\|843075790 |
| 24 | gi\|518517905 |
| 25 | gi\|655094715 |
| 26 | gi\|517805393 |
| 27 | gi\|518469404 |
| 28 | gi\|655084756 |
| 29 | gi\|764415731 |
| 30 | gi\|491699287 |
| 31 | gi\|518251998 |
| 32 | gi\|493730772 |
| 33 | gi\|817723893 |
| 34 | gi\|228697407 |
| 35 | gi\|228736549 |
| 36 | gi\|692165489 |
| 37 | gi\|489315595 |
| 38 | gi\|498015014 |
| 39 | gi\|749037577 |
| 40 | gi\|763303489 |
| 41 | gi\|830323790 |
| 42 | gi\|857573616 |
| 43 | gi\|654951198 |
| 44 | gi\|647569946 |
| 45 | gi\|738784028 |
| 46 | gi\|515717624 |
| 47 | gi\|517613324 |
| 48 | gi\|507035289 |
| 49 | gi\|661257874 |
| 50 | gi\|655116131 |
| 51 | gi\|736161405 |
| 52 | gi\|493687687 |
| 53 | gi\|806498422 |
| 54 | gi\|532550849 |
| 55 | gi\|757435944 |
| 56 | gi\|737448097 |
| 57 | gi\|542116840 |
| 58 | gi\|764608412 |
| 59 | gi\|518088806 |
| 60 | gi\|768926886 |
| 61 | gi\|498013687 |
| 62 | gi\|498020927 |
| 63 | gi\|498487619 |
| 64 | gi\|530665825 |
| 65 | gi\|753200845 |
| 66 | gi\|495633284 |
| 67 | gi\|748815403 |
| 68 | gi\|738932691 |
| 69 | gi\|738896417 |
| 70 | gi\|652405427 |
| 71 | gi\|764371274 |
| 72 | gi\|701527930 |
| 73 | gi\|751587021 |
| 74 | gi\|736758744 |
| 75 | gi\|657859536 |
| 76 | gi\|657039097 |
| 77 | gi\|852221735 |
| 78 | gi\|850337075 |
| 79 | gi\|550547409 |
| 80 | gi\|495772021 |
| 81 | gi\|504454491 |
| 82 | gi\|737572351 |
| 83 | gi\|654483633 |
| 84 | gi\|495911896 |
| 85 | gi\|737423431 |
| 86 | gi\|737423433 |

The recombinant microorganism may be bacteria or fungi. The bacteria may be Gram-positive or Gram-negative bacteria. The Gram-negative bacteria may belong to the family Enterobacteriaceae. The Gram-negative bacteria may belong to the genus *Escherichia*, the genus *Salmonella*, the genus *Xanthomonas*, or the genus *Pseudomonas*. The genus *Escherichia* microorganism may be *E. coli*. The genus *Xanthomonas* microorganism may include *Xanthobacter autotrophicus*. Gram-positive bacteria may belong to the genus *Corynebacterium* or the genus *Bacillus*.

The recombinant microorganism may have a genetic modification that increases the level (activity or protein level) of an enzyme that catalyzes a NADPH production reaction to increase an intracellular NADPH level by the reaction. The genetic modification can be amplification of an endogenous gene or introduction of an exogenous gene. The enzyme may be a protein belonging to EC 1.1.1.49. The enzyme may be glucose-6-phosphate dehydrogenase (G6PD or G6PDH). The recombinant microorganism may further include an exogenous gene encoding G6PDH.

Another aspect provides a composition including the recombinant P450 protein or the variant thereof, which is useful for removing a halogenated methane such as fluorinated methane represented by $CH_nF_{4-n}$ (n is an integer of 0 to 3) in a sample. Unless otherwise specified, the recombinant P450 protein or the variant thereof is the same as described above.

With regard to the composition, fluorinated methane represented by $CH_nF_{4-n}$ may be, $CHF_3$, $CH_2F_2$, $CH_3F$, or $CF_4$. The term "removing" includes reducing of a concentration of fluorinated methane in the sample. The reducing includes complete removal.

With regard to the composition, the recombinant P450 protein or the variant thereof may be in a recombinant microorganism, or the composition can comprise a lysate thereof, or a water-soluble material fraction of the lysate. When in a recombinant microorganism, the bacterial cytochrome P450 or the variant thereof may be expressed from an exogenous gene.

The recombinant microorganism may be bacteria or fungi. The bacteria may be Gram-positive or Gram-negative bacteria. The Gram-negative bacteria may belong to the family Enterobacteriaceae. The Gram-negative bacteria may belong to the genus *Escherichia*, the genus *Salmonella*, the genus *Xanthomonas*, or the genus *Pseudomonas*. The genus *Escherichia* microorganism may be *E. coli*. The genus *Xanthomonas* microorganism may include *Xanthobacter autotrophicus*. Gram-positive bacteria may belong to the genus *Corynebacterium* or the genus *Bacillus*.

Removing fluorinated methane may include cleaving of C—F bonds of fluorinated methane, converting of fluorinated methane into other materials, or reducing of the concentration of fluorinated methane in the sample by intracellular accumulation. The converting may be introducing of a hydrophilic group such as a hydroxyl group into fluorinated methane or introducing of a carbon-carbon double bond or a carbon-carbon triple bond thereto.

With regard to the composition, the sample may be in a liquid or gas state. The sample may be industrial waste water or waste gas.

Still another aspect provides a method of reducing a concentration of fluorinated methane in a sample; the method includes contacting the recombinant P450 protein or the variant thereof with the sample containing fluorinated methane represented by $CH_nF_{4-n}$ (n is an integer of 0 to 3) or other halogenated methane to reduce the concentration of halogenated methane in the sample. Unless otherwise specified, the recombinant P450 protein or the variant thereof is the same as described above.

Contacting of the recombinant P450 protein or the variant thereof with the sample may be performed in a sealed container. The contacting may be gas-liquid contact of contacting a gas sample with a liquid containing the recombinant P450 protein or the variant thereof. Further, the contacting may be liquid-liquid contact of contacting a liquid sample with a liquid containing the recombinant P450 protein or the variant thereof. The liquid-liquid contact includes mixing thereof.

With regard to the method, the recombinant P450 protein or the variant thereof may be in a recombinant microorganism that expresses bacterial cytochrome P450 protein, or a lysate thereof or the water-soluble material fraction of the lysate, or the recombinant P450 protein itself (e.g., isolated protein).

The contacting may be performed in the sealed container under conditions where the recombinant microorganism may survive or be viable. The conditions where the recombinant microorganism may survive or be viable may be conditions where the recombinant microorganism may be allowed to proliferate or to be in a resting state. In this case, the contacting may be culturing of the microorganism in the presence of fluorinated methane. The culturing may be performed under aerobic or anaerobic conditions.

The recombinant microorganism may be bacteria or fungi. The bacteria may be Gram-positive or Gram-negative bacteria. The Gram-negative bacteria may belong to the family Enterobacteriaceae. The Gram-negative bacteria may belong to the genus *Escherichia*, the genus *Salmonella*, the genus *Xanthomonas*, or the genus *Pseudomonas*. The genus *Escherichia* microorganism may be *E. coli*. The genus *Xanthomonas* microorganism may include *Xanthobacter autotrophicus*. Gram-positive bacteria may belong to the genus *Corynebacterium* or the genus *Bacillus*.

With regard to the method, the sample may be in a liquid or gas state. The sample may be industrial waste water or waste gas.

Still another aspect provides the variant of bacterial cytochrome P450 protein and a polynucleotide encoding the same.

The variant may be as described above. For instance, the variant may have an amino acid alteration at an amino acid residue corresponding to position F351 of an amino acid sequence of SEQ ID NO: 6, and may have an activity belonging to EC 1.14.15.1. The variant may have replacement of the amino acid residue at position F351 with a different amino acids, for example, any of the 19 natural amino acids, in camC of P450CAM having the amino acid sequence of SEQ ID NO: 6. The variant may be a F351Y, F351T, F351N, F351Q, F351H, or F351D mutant in camC of P450CAM having the amino acid sequence of SEQ ID NO: 6. In another aspect, the variant may have an amino acid alteration at an amino acid residue corresponding to position N320 of an amino acid sequence of SEQ ID NO: 8, and may have an activity belonging to EC 1.14.14.1. The variant may have replacement of the amino acid residue at the position N320 with other amino acids, for example, any of the other 19 natural amino acids in P450BM3 having the amino acid sequence of SEQ ID NO: 8. The variant be N320W, N320F, N320G, N320P, N320S, or N320E in P450BM3 having the amino acid sequence of SEQ ID NO: 8.

The polynucleotide encoding the variant can be codon optimized for use in various organisms. The polynucleotide encoding the variant may be included in the vector. The vector may be any vector, as long as it is used to introduce the polynucleotide into microorganisms. The vector may be a plasmid or viral vector. The polynucleotide may be operably linked to suitable regulatory sequences.

The recombinant microorganism according to an aspect may be used for removing fluorinated methane represented by $CH_nF_{4-n}$ (or other halogenated methane) in the sample.

The variant of the recombinant P450 protein according to an aspect may be used for removing fluorinated methane in the sample.

The composition including the recombinant P450 protein or the variant thereof according to another aspect may be used for removing fluorinated methane in the sample.

The method of reducing the concentration of fluorinated methane in the sample according to still another aspect may efficiently reduce the concentration of fluorinated methane in the sample. For example, a headspace concentration of fluorinated methane can be reduced, by at least 3, 4, 5, 10, 15, or 20% when measured according to the protocol of any of the Examples below. The activity of the p450 variant can be a multiple of 1.5, 2, 2.5, 3, 3.5, 4, or greater, of the wild-type enzyme (in vitro or in an otherwise genetically identical strain).

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

Hereinafter, the present invention will be described in more detail with reference to Examples. However, these Examples are for illustrative purposes only, and the scope of the present invention is not intended to be limited by these Examples.

Example 1: Recombinant *E. coli* Expressing P450$_{CAM}$ Gene and Removal of Halomethane in Sample by Using the Same In this Example, a recombinant *E. coli* expressing a P450$_{CAM}$ gene was prepared, and an effect of removing halomethane, i.e., $CHF_3$, $CF_4$, or $CHCl_3$ in a sample by using the same was examined.

(1) Preparation of Recombinant *E. coli* Expressing P450$_{CAM}$ Gene

As P450$_{CAM}$ genes, camC, camA, and camB genes were amplified from CAM plasmid of *Pseudomonas putida* PpG786 strain, respectively. camC, camA, and camB genes have nucleotide sequences of SEQ ID NO: 5, SEQ ID NO: 1, and SEQ ID NO: 3, respectively. These genes encode amino acid sequences of SEQ ID NO: 6, SEQ ID NO: 2, and SEQ ID NO: 4, respectively. In detail, *P. putida* PpG786 strain DSM 7162 was cultured in an LB medium at 30° C. under stirring at 230 rpm overnight, and then CAM plasmid was isolated using a total DNA extraction kit (Invitrogen Biotechnology). PCR was performed using the CAM plasmid as a template and a set of primers having nucleotide sequences of SEQ ID NOS: 11 and 12; a set of primers having nucleotide sequences of SEQ ID NOS: 13 and 14; and a set of primers having nucleotide sequences of SEQ ID NOS: 15 and 16 to amplify and obtain camA, camB, and camC genes, respectively.

The camC gene which was amplified by PCR using a set of primers of nucleotide sequences of SEQ ID NOS: 11 and 12 was ligated with pETDuet (Novagen, Cat. No. 71146-3), which was digested with restriction enzymes, NcoI and HindII, using an InFusion Cloning Kit (Clontech Laboratories, Inc.) to prepare a pETDuet-camC vector. Further, the prepared pETDuet-camC vector was digested with restriction enzymes, NdeI and XhoI, and ligated with the amplified camA and the amplified camB gene fragment using the InFusion Cloning Kit (Clontech Laboratories, Inc.) to prepare a pETDuet-camC-camAB vector.

FIG. 1 shows a vector map of the pETDuet-camC-camAB vector.

Next, E. coli BL21 strain was introduced with the prepared pETDuet-camC-camAB vector by a heat shock method, and then cultured on a LB plate containing 100 μg/mL of ampicillin. A strain showing ampicillin resistance was selected. Finally, the strain thus selected was designated as a recombinant E. coli BL21/pETDuet-camC-camAB.

(2) Effect of Removing $CHF_3$ or $CHCl_3$ in Sample by Recombinant E. coli Expressing $P450_{CAM}$ Gene In this section, it was examined whether the $P450_{CAM}$ gene-introduced, E. coli BL21/pETDuet-camC-camAB strain prepared in section (1) affects removal of $CHF_3$ or $CHCl_3$ in a sample. In detail, E. coli BL21/pETDuet-camC-camAB was cultured in a TB medium at 30° C. under stirring at 230 rpm. At $OD_{600}$ of about 0.5, 0.5 mM of IPTG was added thereto, followed by culturing at 25° C. and 230 rpm overnight. The cells were harvested and suspended in an M9 medium supplemented with 4 g/L to a cell density of $OD_{600}$ of 2.5. 10 ml of this cell suspension was added to a 60 ml-serum bottle, and then the bottle was sealed. The terrific broth (TB) medium included 12 g of tryptone, 24 g of yeast extract, 5 g of glycerol, and 89 mM phosphate buffer per 1 L of distilled water. Further, the M9 medium included 6 g of $Na_2HPO_4$, 3 g of $KH_2PO_4$, 0.5 g of NaCl, and 1 g of $NH_4Cl$ per 1 L of distilled water.

Next, gas-phase $CHF_3$ was injected through a rubber stopper of a cap of the serum bottle using a syringe to its headspace concentration of 200 ppm. Further, liquid-phase $CHCl_3$ was injected through the rubber stopper of the cap of the serum bottle using the syringe to its concentration of 0.02 mM in the medium. Thereafter, the serum bottle was incubated for 18 hrs to 152 hrs, while stirring at 30° C. and 200 rpm. Each experiment was performed in triplicate.

At a predetermined time interval during incubation, 0.5 ml of the headspace gas containing no medium in the serum bottle was collected using a 1.0 ml-headspace syringe and injected into GC (Agilent 7890, Palo Alto, Calif., USA). The injected $CHF_3$ or $CHCl_3$ was separated through a CP-PoraBOND Q column (25 m length, 0.32 mm i.d., 5 um film thickness, Agilent), and changes in the $CHF_3$ or $CHCl_3$ concentration were analyzed by mass spectrometry (Agilent 5973, Palo Alto, Calif., USA). As a carrier gas, helium was used, and applied to the column at a flow rate of 1.5 ml/min. GC conditions were as follows: An inlet temperature was 250° C., an initial temperature was maintained at 40° C. for 2 minutes, and temperature was raised to 290° C. at a rate of 20° C./min. MS conditions were as follows: Ionization energy was 70 eV, an interface temperature was 280° C., an ion source temperature was 230° C., and a quadrupole temperature was 150° C.

Figure 2:
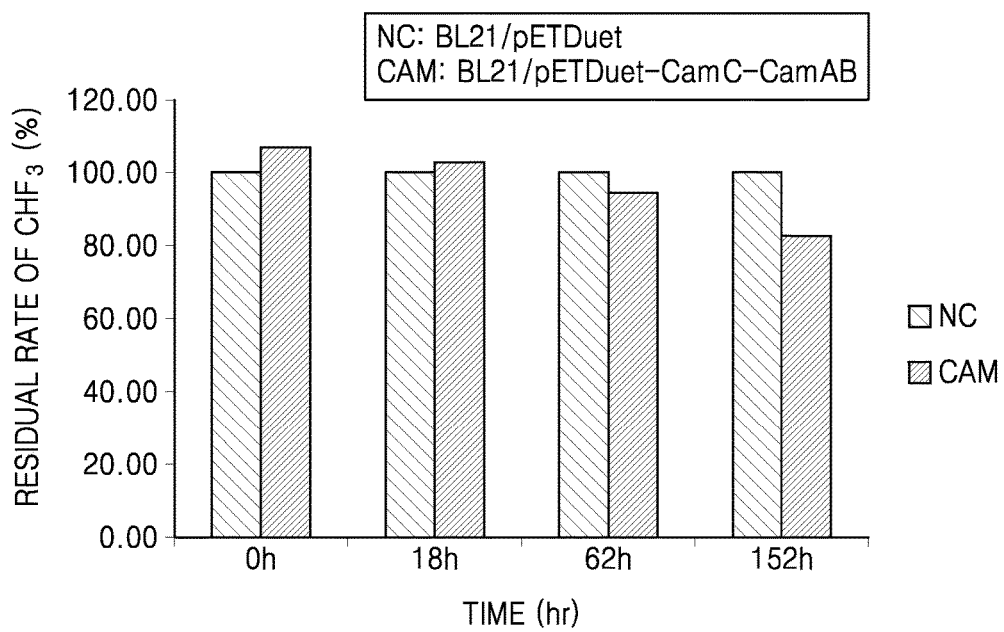
FIG. 2 shows changes in a headspace concentration of $CHF_3$ over time when E. coli BL21/pETDuet-camC-camAB was cultured in a medium contacted with $CHF_3$-containing gas.

FIG. 2 shows changes in a headspace concentration of $CHF_3$ over time when E. coli BL21/pETDuet-camC-camAB was cultured in the medium contacted with $CHF_3$-containing gas.

Figure 3A:
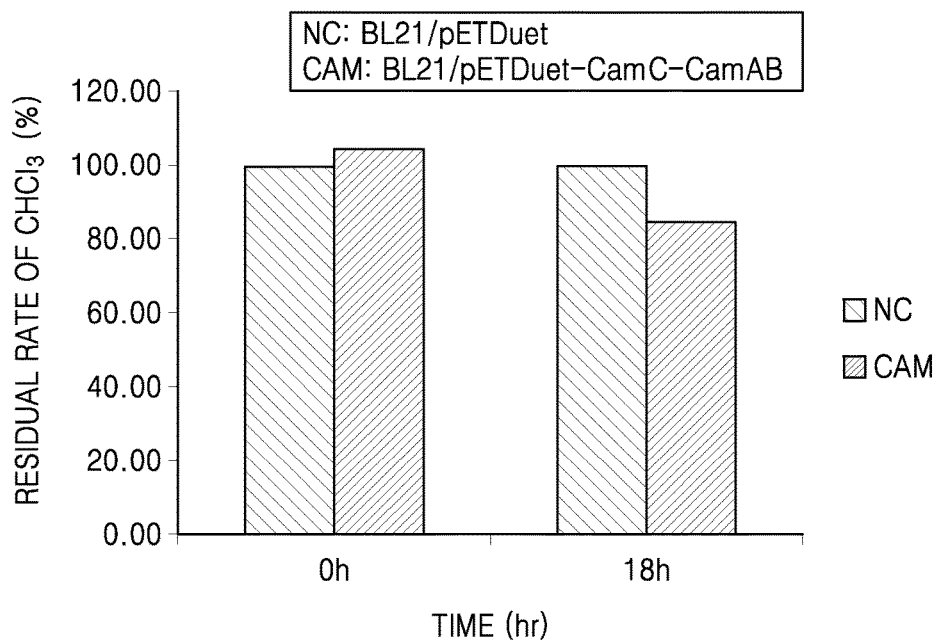
FIG. 3A shows changes in a headspace concentration of $CHCl_3$ over time when E. coli BL21/pETDuet-camC-camAB was cultured in a $CHCl_3$-containing medium.
Figure 3B:
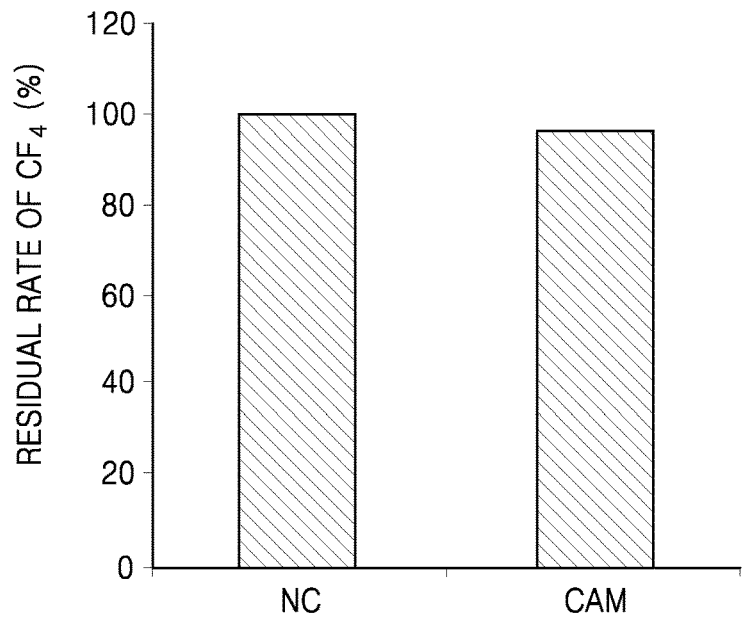
FIG. 3B shows changes in a headspace concentration of $CF_4$ over time when E. coli BL21/pETDuet-camC-camAB was cultured in a medium contacted with $CF_4$-containing gas.

FIG. 3A shows changes in a headspace concentration of $CHCl_3$ over time when E. coli BL21/pETDuet-camC-camAB was cultured in a $CHCl_3$-containing medium. In FIGS. 2, 3A and 3B, NC represents a negative control group, and 'CAM' represents an experiment performed by using E. coli BL21/pETDuet-camC-camAB. As shown in FIG. 2, when the E. coli BL21/pETDuet-camC-camAB was cultured for 62 hours and 152 hours, the headspace concentration of $CHF_3$ was decreased by about 5.6% and about 17.3%, respectively, compared to the control group. Further, as shown in FIG. 3A, when the E. coli BL21/pETDuet-camC-camAB was cultured for 18 hours, the headspace concentration of $CHCl_3$ was decreased by about 14.8%, compared to the control group.

(3) Effect of Removing $CF_4$ in Sample by Recombinant E. coli Expressing $P450_{CAM}$ Gene In this section, it was examined whether the $P450_{CAM}$ gene-introduced, E. coli BL21/pETDuet-camC-camAB strain prepared in section (1) affects removal of $CF_4$ in a sample.

The experiment was performed in the same manner as the procedure performed for $CHF_3$ in Section (2), except that $CF_4$ was used instead of $CHF_3$ and gas-phase $CF_4$ was injected through a rubber stopper of a cap of the serum bottle using a syringe to its headspace concentration of 1000 ppm, and then the serum bottle was incubated for 7 days, while stirring at 30° C. and 200 rpm. The results are as shown in FIG. 3B.

FIG. 3B shows changes in a headspace concentration of $CF_4$ over time when E. coli BL21/pETDuet-camC-camAB was cultured in a medium contacted with $CF_4$-containing gas. As shown in FIG. 3B, when the E. coli BL21/pETDuet-camC-camAB was cultured for 7 days, the headspace concentration of $CF_4$ was decreased by about 3.57%, compared to the control group.

(4) Recombinant E. coli Expressing Mutant $P450_{CAM}$ Gene and Effect of Removing $CF_4$ in Sample Thereby In this section, mutants were prepared in order to improve the activity of removing fluorinated methane in a sample by $P450_{CAM}$. Phenylalanine (hereinafter, referred to as "F351") at position 351 of the amino acid sequence of SEQ ID NO: 6 was replaced by other 19 natural amino acids (hereinafter, referred to as "F351X". Here, X represents 19 natural amino acids other than phenylalanine), and each of the genes encoding the mutants was introduced into E. coli, and their activity of removing $CF_4$ in a sample was examined. camC corresponds to heme domain and F351 is one of conserved amino acids in the amino acid sequences of camC derived from many different species.

(4.1) Preparation of 19 Mutants

Preparation of the F351X mutants of SEQ ID NO: 6 was performed using a QuikChange II Site-Directed Mutagenesis Kit (Agilent Technology, USA). Site-directed mutagenesis using the kit was performed using PfuUltra high-fidelity (HF) DNA polymerase for mutagenic primer-directed replication of both plasmid strands with the highest fidelity. The basic procedure utilized a supercoiled double-stranded DNA (dsDNA) vector with an insert of interest and two synthetic oligonucleotide primers, both containing the desired mutation. The oligonucleotide primers, each complementary to opposite strands of the vector, were extended during temperature cycling by PfuUltra HF DNA polymerase, without primer displacement. Extension of the oligonucleotide primers generated a mutated plasmid containing staggered nicks. Following temperature cycling, the product was treated with Dpn I. The Dpn I endonuclease (target sequence: 5'-Gm$^6$ATC-3') was specific for methylated and hemimethylated DNA and was used to digest the parental DNA template and to select for mutation-containing synthesized DNA. The nicked vector DNA incorporating the desired mutations was then transformed into XL1-Blue supercompetent cells. The sequence identifiers for the primer sets used to produce the mutations are given in the following Table 6.

TABLE 6

| NO. | Mutation type | Primer sequence |
|---|---|---|
| 1 | F351Y | SEQ ID NOS: 21 and 22 |
| 2 | F351T | SEQ ID NOS: 23 and 24 |
| 3 | F351N | SEQ ID NOS: 25 and 26 |
| 4 | F351Q | SEQ ID NOS: 27 and 28 |
| 5 | F351H | SEQ ID NOS: 29 and 30 |
| 6 | F351D | SEQ ID NOS: 31 and 32 |

In detail, PCR was performed using the pETDuet-camC-camAB vector prepared in (1) as a template and each of the primer sets described in Table 6 as a primer and PfuUlta HF DNA polymerase to obtain mutated vectors. These vector products were treated with DpnI to select mutation-containing synthesized DNAs. The vector DNA incorporating the desired mutations was then transformed into XL1-Blue supercompetent cells to clone a pETDuet-camCmt-camAB vector.

Lastly, the cloned pETDuet-camCmt-camAB vector and pETDuet-camCwt-camAB vector were introduced into *E. coli* BL21 strain in the same manner as in (1), and a finally selected strain was designated as recombinant *E. coli* BL21/pETDuet-camCmt-camAB.

(4.2) Effect of Removing $CF_4$ in Sample by Recombinant *E. coli* BL21/pETDuet-camCmt-camAB In this section, it was examined whether the mutant camC gene-introduced, *E. coli* BL21/pETDuet-camCmt-camAB prepared in section (4.1) affects removal of $CF_4$ in a sample.

The experiment was performed in the same manner as the procedure performed for $CHF_3$ in Section (2), except that $CF_4$ was used instead of $CHF_3$ and gas-phase $CF_4$ was injected through a rubber stopper of a cap of the serum bottle using a syringe to a headspace concentration of 1000 ppm, and then the serum bottle was incubated for 6 days, while stirring at 30° C. and 230 rpm. The results are as shown in Table 7.

TABLE 7

| NO. | Mutation type | Residual amount of $CF_4$ (Percentage relative to control group) | Reduction rate of $CF_4$ (Percentage relative to control group) |
|---|---|---|---|
| 1 | F351Y | 91.82 | 8.18 |
| 2 | F351T | 95.42 | 4.58 |
| 3 | F351N | 92.56 | 7.44 |
| 4 | F351Q | 94.12 | 5.88 |
| 5 | F351H | 89.85 | 10.15 |
| 6 | F351D | 94.31 | 5.69 |
| 7 | F351* | 96.43 | 3.57 |

In Table 7, the control group represents *E. coli* introduced with the pETDuet vector instead of the pETDuet-camCmt-camAB vector, and F351* represents wild-type camC.

Further, in this section, the experiment was performed in the same manner as the procedure performed for $CHF_3$ in Section (2), except that 20 mL of mutant camC-introduced *E. coli* BL21/pETDuet-camCmt-camAB ($OD_{600}$=3.0) prepared in Section (4.1) was injected to a 175-mL flask, $CF_4$ was used instead of $CHF_3$, and gas-phase $CF_4$ was injected through a rubber stopper of a cap of the serum bottle using a syringe to a headspace concentration of 1000 ppm, and then the serum bottle was incubated for 6 days, while stirring at 30° C. and 230 rpm. A residual amount of $CF_4$ over time, that is, a remaining percentage (%) of $CF_4$ was examined. The results are shown in FIG. 3C.

Figure 3C:
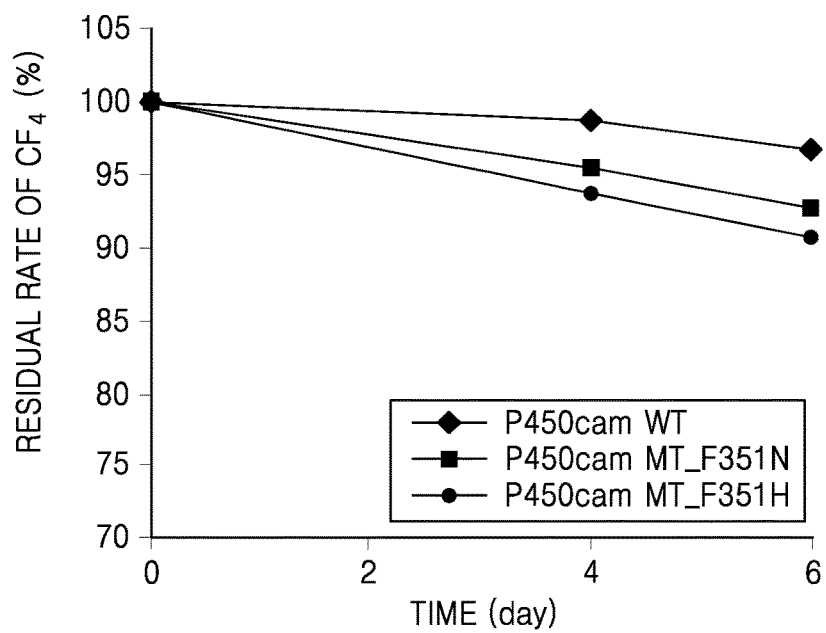
FIG. 3C shows changes of $CF_4$ in a sample over time by E. coli BL21/pETDuet-camCmt-camAB introduced with a mutant camC gene.

FIG. 3C shows changes of $CF_4$ in a sample over time by *E. coli* BL21/pETDuet-camCmt-camAB introduced with the mutant camC gene. As shown in FIG. 3C, when the recombinant *E. coli* P450CAM strain, namely, F351N or F351H mutant gene-containing strain was cultured for 6 days, the $CF_4$ level was further decreased by about 7.02% or about 8.92%, compared to the control group. In contrast, the wild-type strain further decreased the $CF_4$ level by about 3.14%, compared to the control group.

Example 2: Recombinant *E. coli* Expressing $P450_{BM3}$ Gene and Removal of Halomethane in Sample by Using the Same In this Example, a recombinant *E. coli* expressing a $P450_{BM3}$ gene was prepared, and an effect of removing halomethane, i.e., $CHF_3$, $CF_4$, or $CHCl_3$ in a sample by using the same was examined.

Figure 4:
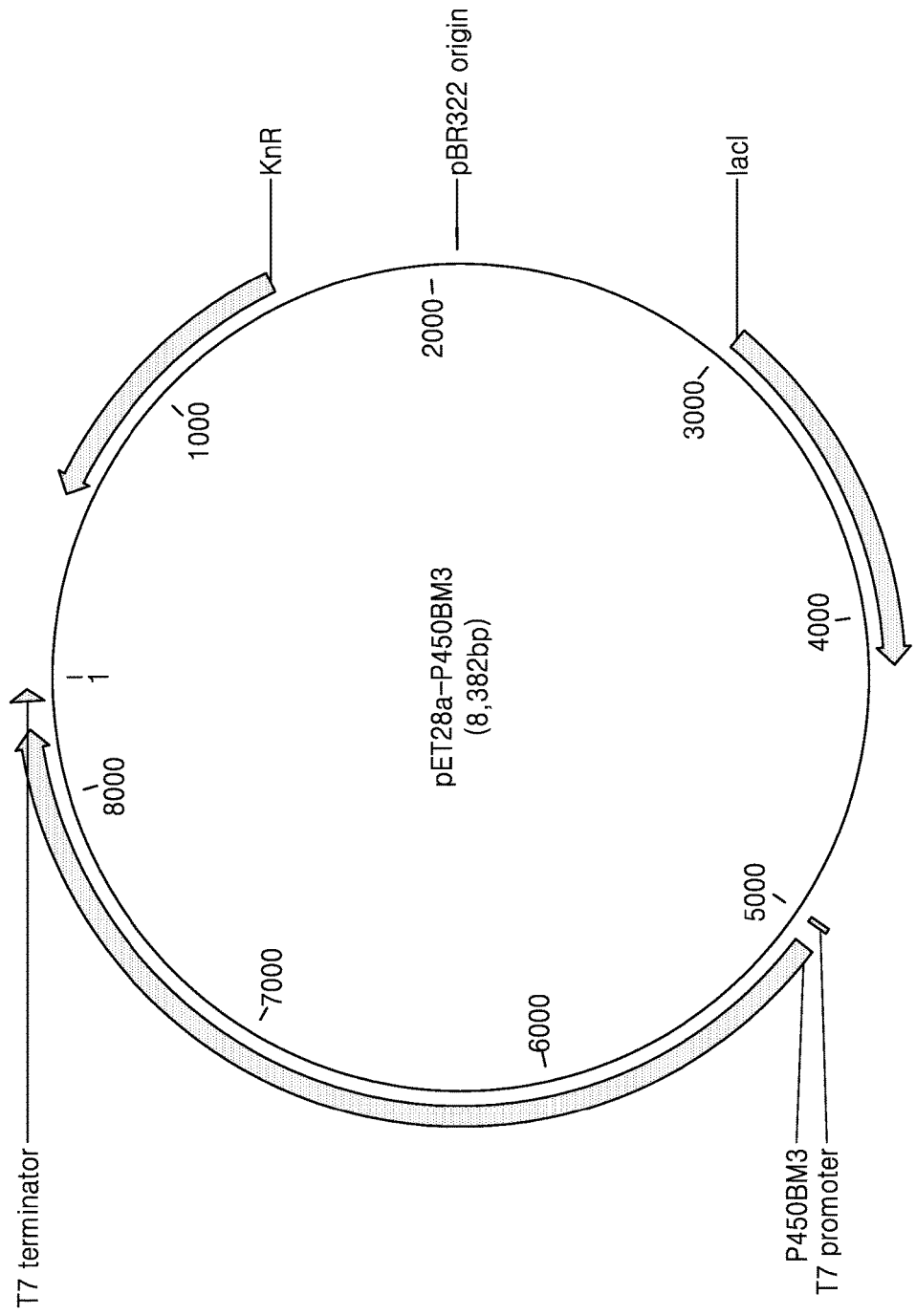
FIG. 4 shows a vector map of a pET28a-P450$_{BM3}$ vector.

(1) Preparation of Recombinant *E. coli* Expressing P450BM3 Gene $P450_{BM3}$ gene of *Bacillus megaterium* (ATCC 14581) strain was amplified. $P450_{BM3}$ gene has a nucleotide sequence of SEQ ID NO: 7, and encodes an amino acid sequence of SEQ ID NO: 8. In detail, *B. megaterium* (ATCC 14581) was cultured in an LB medium at 30° C. under stirring at 230 rpm overnight, and then a genomic DNA was isolated using the total DNA extraction kit (Invitrogen Biotechnology). PCR was performed using this genomic DNA as a template and a set of primers having nucleotide sequences of SEQ ID NOS: 17 and 18 to amplify and obtain the $P450_{BM3}$ gene. The $P450_{BM3}$ gene thus amplified was ligated with pET28a (Novagen, Cat. No. 69864-3), which was digested with restriction enzymes, NcoI and XhoI, using the InFusion Cloning Kit (Clontech Laboratories, Inc.) to prepare a pET28a-$P450_{BM3}$ vector. FIG. 4 shows a vector map of the pET28a-$P450_{BM3}$ vector.

Further, in order to increase an intracellular NADPH level, a zwf gene encoding glucose 6-phosphate dehydrogenase of *E. coli* K12 (MG1655) was amplified. The Zwf gene has a nucleotide sequence of SEQ ID NO: 9, and encodes an amino acid sequence of SEQ ID NO: 10. In detail, *E. coli* was cultured in an LB medium at 37° C. under stirring at 230 rpm overnight, and then a genomic DNA was isolated using the total DNA extraction kit (Invitrogen Biotechnology). PCR was performed using this genomic DNA as a template and a set of primers having nucleotide sequences of SEQ ID NOS: 19 and 20 to amplify and obtain the zwf gene. The zwf gene thus amplified was ligated with pACYCDuet (Novagen, Cat. No. 71147-3), which was digested with restriction enzymes, NcoI and SacI, using the InFusion Cloning Kit (Clontech Laboratories, Inc.) to prepare a pACYCDuet-zwf vector.

Figure 5:
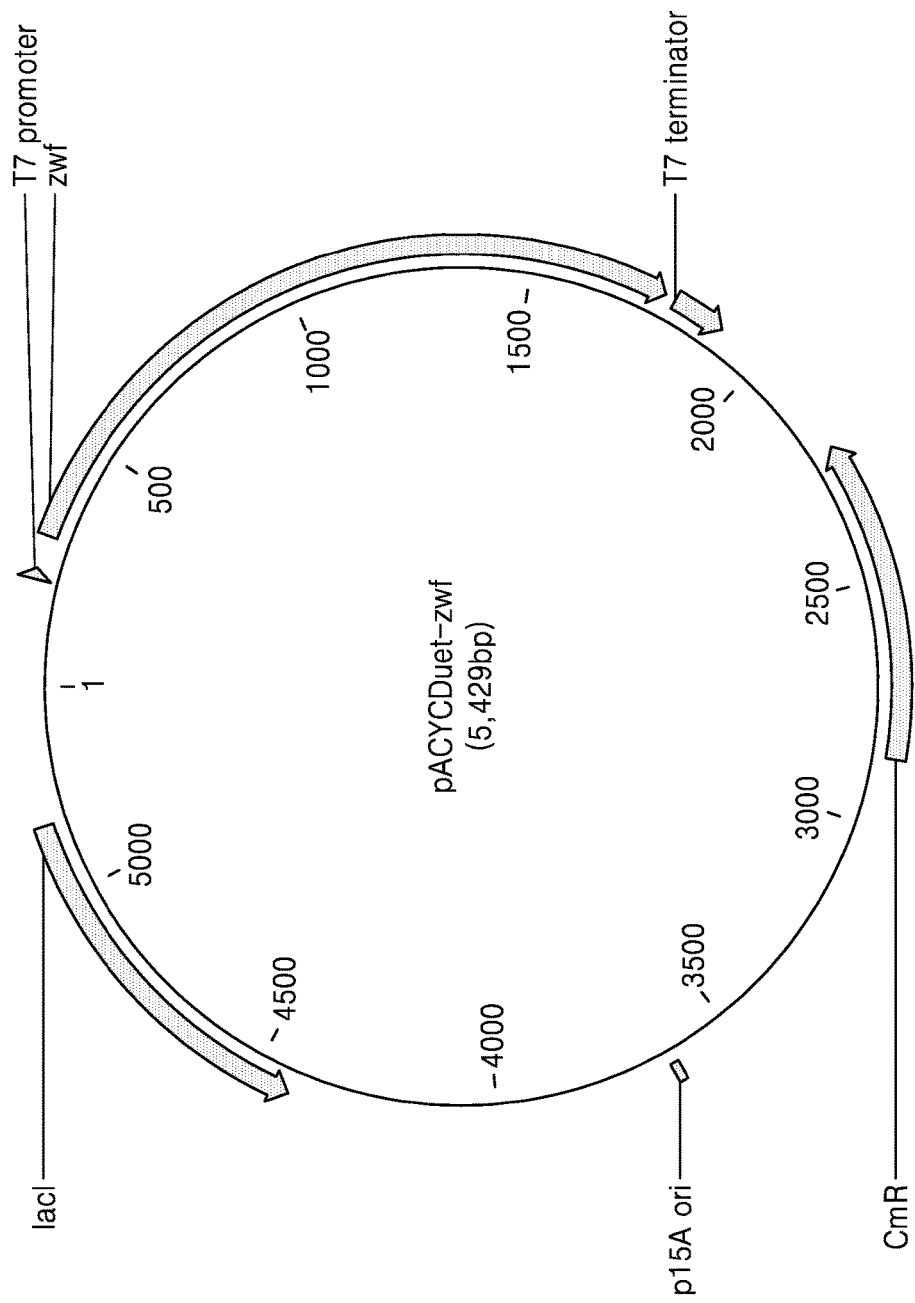
FIG. 5 shows a vector map of a pACYCDuet-zwf vector.

FIG. 5 shows a vector map of the pACYCDuet-zwf vector.

Next, *E. coli* BL21 strain was introduced with the prepared pET28a-$P450_{BM3}$ vector by a heat shock method, and then cultured on a LB plate containing 50 µg/mL of kanamycin. A strain showing kanamycin resistance was selected. Finally, the strain thus selected was designated as a recombinant *E. coli* BL21/pET28a-$P450_{BM3}$.

Further, *E. coli* BL21 strain was introduced with the prepared pET28a-$P450_{BM3}$ vector and pACYCDuet-zwf vector by a heat shock method, and then cultured on a LB plate containing 50 µg/mL of kanamycin and 35 µg/mL of chloramphenicol. A strain showing kanamycin resistance and chloramphenicol resistance was selected. Finally, the strain thus selected was designated as a recombinant *E. coli* BL21/pET28a-P450$_{BM3}$+pACYCDuet-zwf.

(2) Effect of Removing CHF$_3$ or CHCl$_3$ in Sample by Recombinant *E. coli* Expressing P450$_{BM3}$ Gene In this section, it was examined whether the P450$_{BM3}$ gene-introduced, recombinant *E. coli* BL21/pET28a-P450BM3 strain or BL21/pET28a-P450$_{BM3}$+pACYCDuet-zwf strain prepared in section (1) affects removal of CHF$_3$ or CHCl$_3$ in a sample.

In detail, *E. coli* BL21/pET28a-P450$_{BM3}$ or BL21/pET28a-P450$_{BM3}$+pACYCDuet-zwf strain was cultured in the TB medium at 30° C. under stirring at 230 rpm. At OD$_{600}$ of about 0.5, 0.2 mM of IPTG was added thereto, followed by culturing at 25° C. and 230 rpm overnight. The cells were harvested and suspended in the M9 medium to a cell density of OD$_{600}$ of 2.5. 10 ml of this cell suspension was added to a 60 ml-serum bottle, and then the bottle was sealed. The TB medium and the M9 medium are the same as those described in Example 1.

Next, gas-phase CHF$_3$ was injected through a rubber stopper of a cap of the serum bottle using a syringe to a headspace concentration of 200 ppm. Further, liquid-phase CHCl$_3$ was injected through the rubber stopper of the cap of the serum bottle using the syringe to its concentration of 0.02 mM in the medium. Thereafter, the serum bottle was incubated for 15 hrs to 142 hrs, while stirring at 30° C. and 230 rpm. Each experiment was performed in triplicate.

At a predetermined time interval during incubation, the headspace concentration of CHCl$_3$ or CHCl$_3$ in the serum bottle was analyzed under the same conditions as described in (2) of Example 2.

Figure 6:
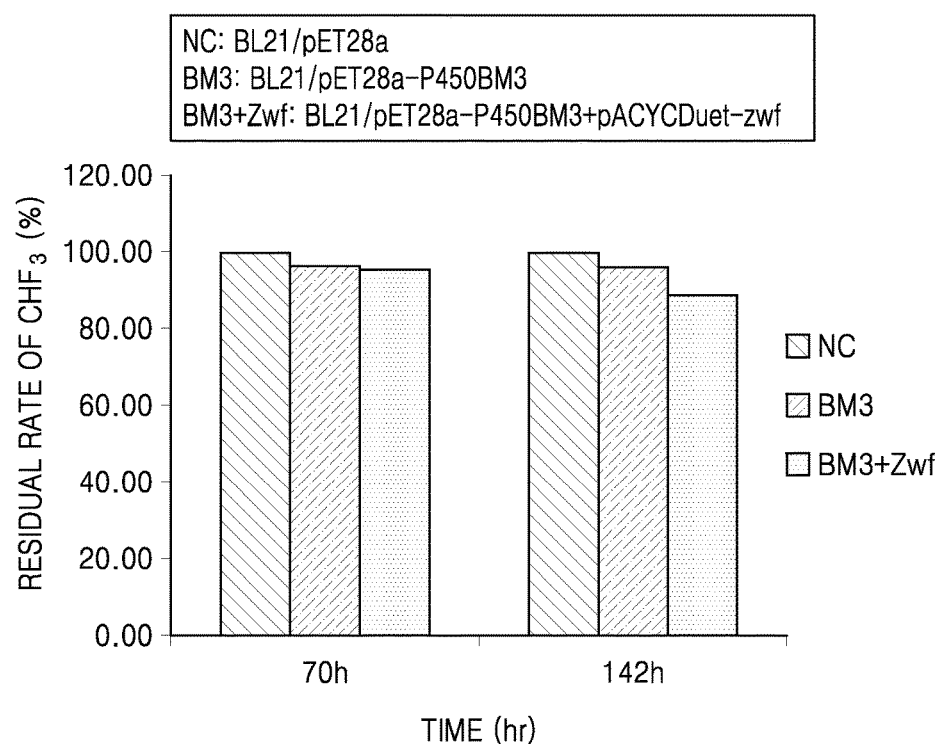
FIG. 6 shows changes in a headspace concentration of $CHF_3$ over time when recombinant E. coli BL21/pET28a-P450$_{BM3}$ or recombinant E. coli BL21/pET28a-P450$_{BM3}$+pACYCDuet-zwf was cultured in a solution contacted with $CHF_3$-containing gas.

FIG. 6 shows changes in headspace concentration of CHF$_3$ over time when *E. coli* BL21/pET28a-P450$_{BM3}$ or BL21/pET28a-P450$_{BM3}$+pACYCDuet-zwf was cultured for 142 hours in a medium contacted with CHF$_3$-containing gas.

Figure 7:
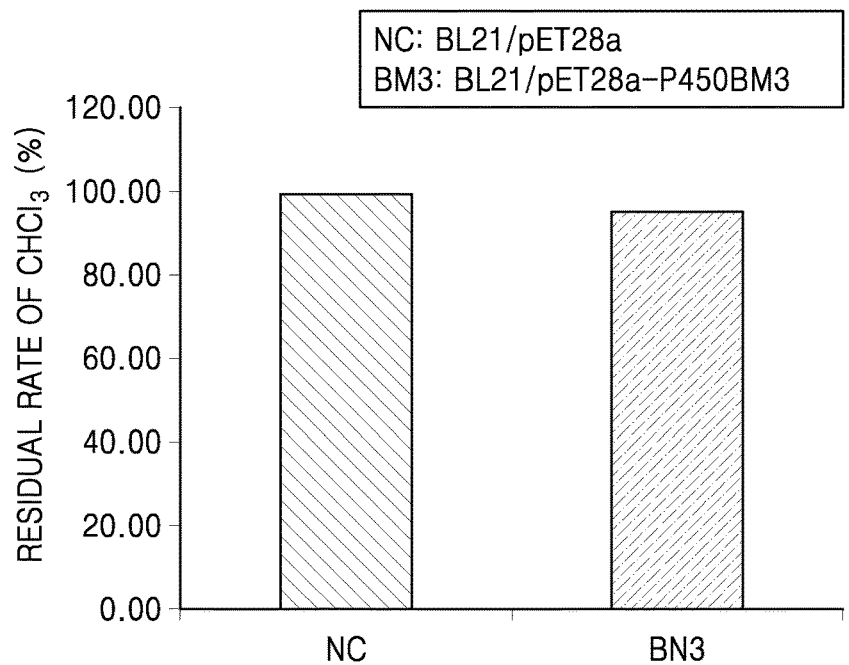
FIG. 7 shows changes in a headspace concentration of $CHCl_3$ over time when E. coli BL21/pET28a-P450$_{BM3}$ was cultured in a $CHCl_3$-containing solution.
Figure 8:
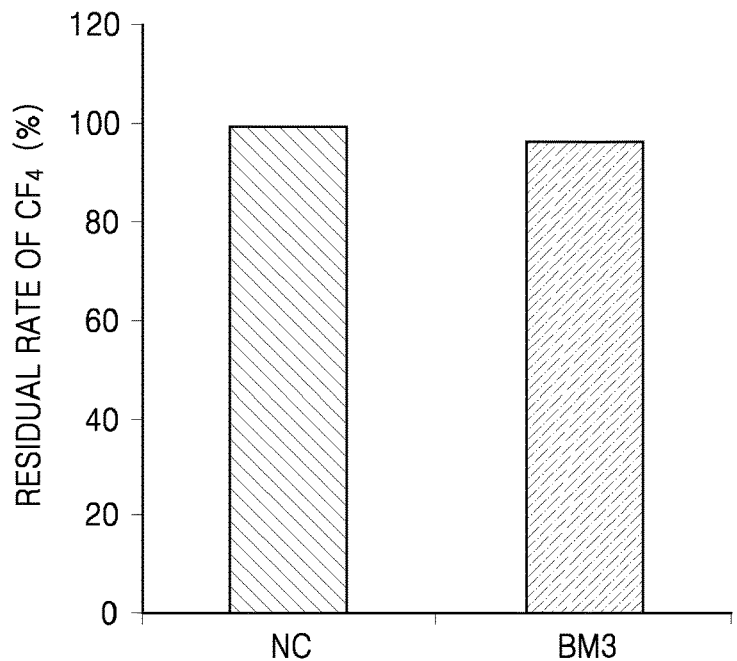
FIG. 8 shows changes in a headspace concentration of $CF_4$ over time when E. coli BL21/pET28a-P450$_{BM3}$ was cultured for 7 days in a medium contacted with $CF_4$-containing gas.

FIG. 7 shows changes in headspace concentration of CHCl$_3$ over time when *E. coli* BL21/pET28a-P450$_{BM3}$ was cultured for 15 hours in a CHCl$_3$-containing medium. In FIGS. 6, 7, and 8, NC represents a negative control group, 'BM3' represents an experiment performed by using *E. coli* BL21/pET28a-P450$_{BM3}$, and 'BM3+Zwf' represents an experiment performed by using *E. coli* BL21/pET28a-P450$_{BM3}$+pACYCDuet-zwf. As shown in FIG. 6, when the *E. coli* BL21/pET28a-P450$_{BM3}$ and *E. coli* BL21/pET28a-P450$_{BM3}$+pACYCDuet-zwf were cultured for 70 hours and 142 hours, the headspace concentration of CHF$_3$ was decreased, compared to the control group, by about 3.93% and about 4.57% upon culturing for 70 hours and by about 4.15% and about 11.03% upon culturing for 142 hours, respectively. Further, as shown in FIG. 7, when they were cultured for 15 hours, the headspace concentration of CHCl$_3$ was decreased by about 4.1%, compared to the control group.

(3) Effect of Removing CF$_4$ in Sample by Recombinant *E. coli* Expressing P450$_{BM3}$ Gene In this section, it was examined whether the P450$_{BM3}$ gene-introduced, *E. coli* BL21/pET28a-P450$_{BM3}$ strain prepared in section (1) affects removal of CF$_4$ in a sample.

The experiment was performed in the same manner as the procedure performed for CHF$_3$ in Section (2), except that CF$_4$ was used instead of CHF$_3$ and gas-phase CF$_4$ was injected through a rubber stopper of a cap of the serum bottle using a syringe to its headspace concentration of 1000 ppm, and then the serum bottle was incubated for 7 days, while stirring at 30° C. and 200 rpm. The results are as shown in FIG. 8.

FIG. 8 shows changes in a headspace concentration of CF$_4$ over time when *E. coli* BL21/pET28a-P450$_{BM3}$ was cultured for 7 days in a medium contacted with CF$_4$-containing gas. As shown in FIG. 8, when the *E. coli* BL21/pET28a-P450$_{BM3}$ was cultured for 7 days, the headspace concentration of CF$_4$ was decreased by about 3.03%, compared to the control group.

(4) Recombinant *E. coli* Expressing Mutant P450$_{BM3}$ Gene and Effect of Removing CF$_4$ in Sample Thereby In this section, mutants were prepared in order to improve the activity of removing fluorinated methane in a sample by P450$_{BM3}$. Asparagine (hereinafter, referred to as "N320") at position 320 of the amino acid sequence of SEQ ID NO: 8 was replaced by other 19 natural amino acids (hereinafter, referred to as "N320X". Here, X represents 19 natural amino acids other than asparagine), and each of the genes encoding the mutants was introduced into *E. coli*, and their activity of removing CF$_4$ in a sample was examined. N320 is included in the heme-containing P450 oxygenase domain, and N320 is one of conserved amino acids in the amino acid sequences of enzymes having the same function.

(4.1) Preparation of 19 Mutants

Preparation of the N320X mutants of SEQ ID NO: 8 was performed using a QuikChange II Site-Directed Mutagenesis Kit (Agilent Technology, USA). Mutagenesis using the kit was performed in the same manner as described above.

Of respective primer sets used to induce N320X mutation, primer sets regarding to the increased activity of removing fluorinated methane in a sample, compared to that of the wild-type *E. coli*, are given in the following Table 8.

TABLE 8

| NO. | Mutation type | Primer sequence |
|---|---|---|
| 1 | N320W | SEQ ID NOS: 33 and 34 |
| 2 | N320F | SEQ ID NOS: 35 and 36 |
| 3 | N320G | SEQ ID NOS: 37 and 38 |
| 4 | N320P | SEQ ID NOS: 39 and 40 |
| 5 | N320S | SEQ ID NOS: 41 and 42 |
| 6 | N320E | SEQ ID NOS: 43 and 44 |

In detail, PCR was performed using the pET28a-P450BM3 vector prepared in (1) as a template and each of the primer sets described in Table 8 as a primer and PfuUlta HF DNA polymerase to obtain mutated vectors. These vector products were treated with DpnI to select mutation-containing synthesized DNAs. The vector DNA incorporating the desired mutations was then transformed into XL1-Blue supercompetent cells to clone a pET28a-P450BM3mt vector.

Lastly, the cloned pET28a-P450$_{BM3}$ vector and pET28a-P450BM3mt vector were introduced into *E. coli* BL21 strain in the same manner as in (1), and a finally selected strain was designated as recombinant *E. coli* BL21/pET28a-P450BM3mt.

(4.2) Effect of Removing CF$_4$ in Sample by Recombinant *E. coli* BL21/pET28a-P450BM3mt In this section, it was examined whether the mutant P450BM3mt-introduced, *E. coli* BL21/pET28a-P450BM3mt prepared in section (4.1) affects removal of CF$_4$ in a sample.

The experiment was performed in the same manner as the procedure performed for CHF$_3$ in Section (2), except that CF$_4$ was used instead of CHF$_3$ and gas-phase CF$_4$ was injected through a rubber stopper of a cap of the serum bottle using a syringe to a headspace concentration of 1000 ppm, and then the serum bottle was incubated for 6 days, while stirring at 30° C. and 230 rpm. The results are as shown in Table 9.

TABLE 9

| NO. | Mutation type | Residual amount of $CF_4$ (Percentage relative to control group) | Reduction rate of $CF_4$ (Percentage relative to control group) |
|---|---|---|---|
| 1 | N320W | 94.42 | 5.58 |
| 2 | N320F | 87.38 | 12.62 |
| 3 | N320G | 89.82 | 10.18 |
| 4 | N320P | 86.89 | 13.11 |
| 5 | N320S | 82.03 | 17.97 |
| 6 | N320E | 88.48 | 11.52 |
| 7 | N320* | 96.97 | 3.03 |

In Table 9, the control group represents *E. coli* introduced with the pET28a vector instead of the pET28a-P450BM3mt vector, and N320* represents wild-type P450BM3.

Further, in this section, the experiment was performed in the same manner as the procedure performed for $CHF_3$ in Section (2), except that 100 mL of mutant P450BM3-introduced *E. coli* BL21/pET28a-P450BM3mt ($OD_{600}$=3.0) prepared in Section (4.1) was injected to a 250-mL flask, $CF_4$ was used instead of $CHF_3$, and gas-phase $CF_4$ was injected through a rubber stopper of a cap of the serum bottle using a syringe to its headspace concentration of 1000 ppm, and then the serum bottle was incubated for 48 hours, while stirring at 30° C. and 230 rpm. Culturing was performed in the same manner as for $CHF_3$, and a residual amount of $CF_4$ over time, that is, a remaining percentage (%) of $CF_4$ was examined. The results are shown in FIG. 9.

Figure 9:
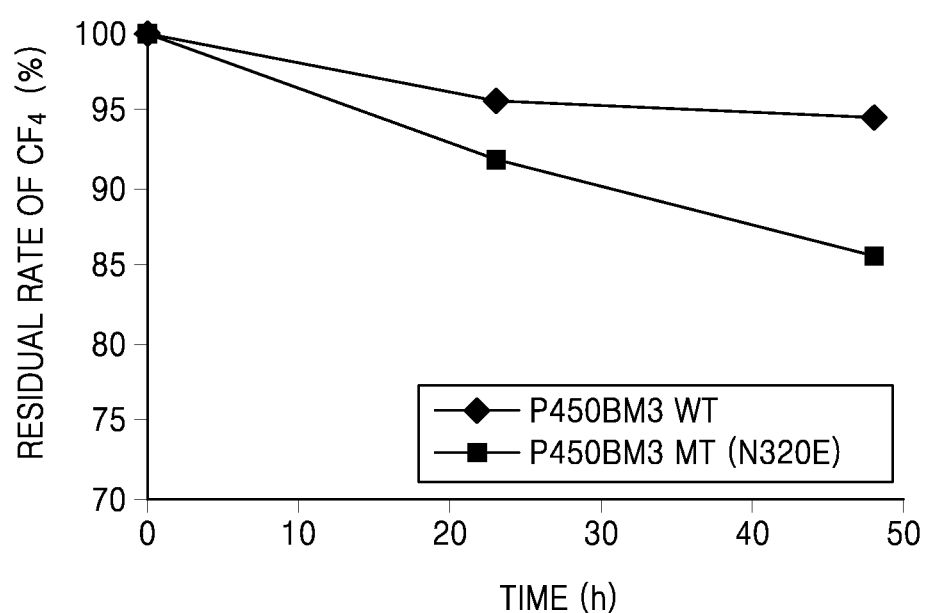
FIG. 9 shows changes in a concentration of $CF_4$ in a sample over time by E. coli BL21/pET28a-P450BM3mt introduced with a mutant P450BM3 gene.

FIG. 9 shows changes of $CF_4$ in a sample over time by *E. coli* BL21/pET28a-P450BM3mt introduced with the mutant P450BM3 gene. As shown in FIG. 9, when the recombinant *E. coli* P450BM3 strain, namely, N320E mutant gene-containing strain was cultured for 48 hours, the $CF_4$ level was further decreased by about 14.3%, compared to the control group. In contrast, the wild-type strain further decreased the $CF_4$ level by about 5.5%, compared to the control group.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A bacterial P450Cam variant polypeptide having an amino acid alteration at an amino acid residue corresponding to position F351 of SEQ ID NO: 6 selected from the group consisting of F351T, F351N, F351Q, and F351D and having an activity belonging to EC 1.14.15.1.

2. The variant polypeptide of claim 1, wherein the variant polypeptide comprises a P450Cam variant comprising SEQ ID NO: 6 with a substitution at position F351 of SEQ ID NO: 6, wherein the substitution is F351T, F351N, F351Q, or F351D.

3. A composition comprising the P450Cam variant of claim 1.

4. A polynucleotide encoding the bacterial P450Cam variant polypeptide of claim 1.

5. A recombinant microorganism comprising an exogenous gene encoding the bacterial P450Cam variant polypeptide of claim 1.

6. The recombinant microorganism of claim 5, wherein the exogenous gene encodes a P450Cam variant polypeptide comprising SEQ ID NO: 6 with a substitution at position F351 of SEQ ID NO: 6, wherein the substitution is F351T, F351N, F351Q, or F351D.

7. The recombinant microorganism of claim 5, further comprising an exogenous gene encoding a protein having an activity belonging to EC 1.1.1.49.

8. A method of reducing a concentration of fluorinated methane in a sample, the method comprising contacting a recombinant P450 protein, or a P450Cam variant polypeptide having an amino acid alteration at an amino acid residue corresponding to position F351 of SEQ ID NO: 6 and having an activity belonging to EC 1.14.15.1, with the sample comprising fluorinated methane represented by $CH_nF4-n$ (n is an integer of 0 to 3) to reduce the concentration of fluorinated methane in the sample.

9. The method of claim 8, wherein the contacting is performed in a sealed container.

10. A method of reducing a concentration of fluorinated methane in a sample, the method comprising contacting a recombinant microorganism with the sample comprising fluorinated methane represented by $CH_nF4-n$ (n is an integer of 0 to 3) to reduce the concentration of fluorinated methane in the sample, wherein the recombinant microorganism comprises an exogenous gene encoding a bacterial P450 protein or a variant thereof, wherein the variant is a P450Cam variant having an amino acid alteration at an amino acid residue corresponding to position F351 of SEQ ID NO: 6 and having an activity belonging to EC 1.14.15.1.

11. The method of claim 10, wherein the contacting is performed in a sealed container where the recombinant microorganism survives or is viable.

12. The method of claim 10, wherein the contacting comprises culturing the recombinant microorganism in the presence of the sample.

13. The method of claim 10, wherein the sample is industrial waste water or waste gas.

14. The method of claim 10, wherein the recombinant microorganism further comprises an exogenous gene encoding a protein having an activity belonging to EC 1.1.1.49.

15. The method of claim 10, wherein the recombinant microorganism comprises an exogenous gene encoding the P450Cam variant comprising a F351Y, F351T, F351N, F351Q, F351H, or F351D mutation.

16. A bacterial P450BM3 variant polypeptide having an amino acid alteration at an amino acid residue corresponding to position N320 of SEQ ID NO: 8 and having an activity belonging to EC 1.14.14.1.

17. The variant polypeptide of claim 16, wherein the variant polypeptide comprises a P450BM3 variant comprising SEQ ID NO: 8 with a substitution at position N320.

18. The composition of claim 17, wherein the substitution at amino acid position N320 is a N320W, N320F, N320G, N320P, N320S, or N320E mutation.

19. A composition comprising the P450BM3 variant polypeptide of claim 16.

20. A polynucleotide encoding the bacterial P450BM3 variant polypeptide of claim 16.

21. A recombinant microorganism comprising an exogenous gene encoding the bacterial P450BM3 variant polypeptide of claim 16.

22. The recombinant microorganism of claim 21, wherein the exogenous gene encodes a P450BM3 variant polypeptide comprising SEQ ID NO: 8 with a substitution at position N320.

23. The recombinant microorganism of claim 22, wherein the substitution at position N320 is N320W, N320F, N320G, N320P, N320S, or N320E.

24. The recombinant microorganism of claim 21, further comprising an exogenous gene encoding a protein having an activity belonging to EC 1.1.1.49.

25. A method of reducing a concentration of fluorinated methane in a sample, the method comprising contacting a P450BM3 variant polypeptide of claim 16 with the sample comprising fluorinated methane represented by CHnF4-n (n is an integer of 0 to 3) to reduce the concentration of fluorinated methane in the sample.

26. The method of claim 25, wherein the contacting is performed in a sealed container.

27. A method of reducing a concentration of fluorinated methane in a sample, the method comprising contacting the recombinant microorganism of claim 21 with a sample comprising fluorinated methane represented by CHnF4-n (n is an integer of 0 to 3) to reduce the concentration of fluorinated methane in the sample.

28. The method of claim 27, wherein the contacting is performed in a sealed container where the recombinant microorganism survives or is viable.

29. The method of claim 27, wherein the contacting comprises culturing the recombinant microorganism in the presence of the sample.

30. The method of claim 27, wherein the sample is industrial waste water or waste gas.

31. The method of claim 27, wherein the recombinant microorganism further comprises an exogenous gene encoding a protein belonging to EC 1.1.1.49.

* * * * *

SEQUENCE LISTING

```
<160> NUMBER OF SEQ ID NOS: 56

<210> SEQ ID NO 1
<211> LENGTH: 1269
<212> TYPE: DNA
<213> ORGANISM: Pseudomonas putida
<220> FEATURE:
<221> NAME/KEY: misc_feature
<222> LOCATION: (1)..(1269)
<223> OTHER INFORMATION: PpG786 strain DSM 7162

<400> SEQUENCE: 1
atgaacgcaa acgacaacgt ggtcatcgtc ggtaccggac tggctggcgt tgaggtcgcc      60
ttcggcctgc gcgccagcgg ctgggaaggc aatatccggt tggtggggga tgcgacggta     120
attccccatc acctaccacc gctatccaaa gcttacttgg ccggcaaagc cacagcggaa     180
agcctgtacc tgagaacccc agatgcctat gcagcgcaga acatccaact actcggaggc     240
acacaggtaa cggctatcaa ccgcgaccga cagcaagtaa tcctatcgga tggccgggca     300
ctggattacg accggctggt attggctacc ggagggcgtc caagaccccct accggtggcc     360
```

```
agtggcgcag ttggaaaggc gaacaacttt cgatacctgc gcacactcga ggacgccgag    420
tgcattcgcc ggcagctgat tgcggataac cgtctggtgg tgattggtgg cggctacatt    480
ggccttgaag tggctgccac cgccatcaag gcgaacatgc acgtcaccct gcttgatacg    540
gcagcccggg ttctggagcg ggttaccgcc ccgccggtat cggccttttc gagcaccta    600 caccgcgaag ccggcgttga catacgaacc ggcacgcagg tgtgcgggtt cgagatgtcg    660
accgaccaac agaaggttac tgccgtcctc tgcgaggacg gcacaaggct gccagcggat    720
ctggtaatcg ccgggattgg cctgatacca aactgcgagt tggccagtgc ggccggcctg    780
caggttgata acggcatcgt gatcaacgaa cacatgcaga cctctgatcc cttgatcatg    840
gccgtcggcg actgtgcccg atttcacagt cagctctatg accgctgggt gcgtatcgaa    900
tcggtgccca atgccttgga gcaggcacga agatcgccg ccatcctctg tgcaaggtg    960 ccacgcgatg aggcggcgcc ctggttctgg tccgatcagt atgagatcgg attgaagatg    1020
gtcggactgt ccgaagggta cgaccggatc attgtccgcg gctctttggc gcaacccgac    1080
ttcagcgttt tctacctgca gggagaccgg gtattggcgg tcgatacagt gaaccgtcca    1140
gtggagttca accagtcaaa acaaataatc acggatcgtt tgccggttga accaaaccta    1200
ctcggtgacg aaagcgtgcc gttaaaggaa atcatcgccg ccgccaaagc tgaactgagt    1260
agtgcctaa                                                             1269
```

<210> SEQ ID NO 2
<211> LENGTH: 422
<212> TYPE: PRT
<213> ORGANISM: Pseudomonas putida
<220> FEATURE:
<221> NAME/KEY: misc_feature
<222> LOCATION: (1)..(422)
<223> OTHER INFORMATION: PpG786 strain DSM 7162

<400> SEQUENCE: 2

```
Met Asn Ala Asn Asp Asn Val Val Ile Val Gly Thr Gly Leu Ala Gly
1               5                   10                  15

Val Glu Val Ala Phe Gly Leu Arg Ala Ser Gly Trp Glu Gly Asn Ile
                20                  25                  30

Arg Leu Val Gly Asp Ala Thr Val Ile Pro His His Leu Pro Pro Leu
            35                  40                  45

Ser Lys Ala Tyr Leu Ala Gly Lys Ala Thr Ala Glu Ser Leu Tyr Leu
        50                  55                  60

Arg Thr Pro Asp Ala Tyr Ala Ala Gln Asn Ile Gln Leu Leu Gly Gly
65                  70                  75                  80

Thr Gln Val Thr Ala Ile Asn Arg Asp Arg Gln Gln Val Ile Leu Ser
                85                  90                  95

Asp Gly Arg Ala Leu Asp Tyr Asp Arg Leu Val Leu Ala Thr Gly Gly
            100                 105                 110

Arg Pro Arg Pro Leu Pro Val Ala Ser Gly Ala Val Gly Lys Ala Asn
        115                 120                 125

Asn Phe Arg Tyr Leu Arg Thr Leu Glu Asp Ala Glu Cys Ile Arg Arg
    130                 135                 140

Gln Leu Ile Ala Asp Asn Arg Leu Val Val Ile Gly Gly Gly Tyr Ile
145                 150                 155                 160

Gly Leu Glu Val Ala Ala Thr Ala Ile Lys Ala Asn Met His Val Thr
                165                 170                 175

Leu Leu Asp Thr Ala Ala Arg Val Leu Glu Arg Val Thr Ala Pro Pro
            180                 185                 190
```

```
Val Ser Ala Phe Tyr Glu His Leu His Arg Glu Ala Gly Val Asp Ile
        195                 200                 205

Arg Thr Gly Thr Gln Val Cys Gly Phe Glu Met Ser Thr Asp Gln Gln
    210                 215                 220

Lys Val Thr Ala Val Leu Cys Glu Asp Gly Thr Arg Leu Pro Ala Asp
225                 230                 235                 240

Leu Val Ile Ala Gly Ile Gly Leu Ile Pro Asn Cys Glu Leu Ala Ser
                245                 250                 255

Ala Ala Gly Leu Gln Val Asp Asn Gly Ile Val Ile Asn Glu His Met
            260                 265                 270

Gln Thr Ser Asp Pro Leu Ile Met Ala Val Gly Asp Cys Ala Arg Phe
        275                 280                 285

His Ser Gln Leu Tyr Asp Arg Trp Val Arg Ile Glu Ser Val Pro Asn
    290                 295                 300

Ala Leu Glu Gln Ala Arg Lys Ile Ala Ala Ile Leu Cys Gly Lys Val
305                 310                 315                 320

Pro Arg Asp Glu Ala Ala Pro Trp Phe Trp Ser Asp Gln Tyr Glu Ile
                325                 330                 335

Gly Leu Lys Met Val Gly Leu Ser Glu Gly Tyr Asp Arg Ile Ile Val
            340                 345                 350

Arg Gly Ser Leu Ala Gln Pro Asp Phe Ser Val Phe Tyr Leu Gln Gly
        355                 360                 365

Asp Arg Val Leu Ala Val Asp Thr Val Asn Arg Pro Val Glu Phe Asn
    370                 375                 380

Gln Ser Lys Gln Ile Ile Thr Asp Arg Leu Pro Val Glu Pro Asn Leu
385                 390                 395                 400

Leu Gly Asp Glu Ser Val Pro Leu Lys Glu Ile Ile Ala Ala Ala Lys
                405                 410                 415

Ala Glu Leu Ser Ser Ala
            420

<210> SEQ ID NO 3
<211> LENGTH: 324
<212> TYPE: DNA
<213> ORGANISM: Pseudomonas putida
<220> FEATURE:
<221> NAME/KEY: misc_feature
<222> LOCATION: (1)..(324)
<223> OTHER INFORMATION: PpG786 strain DSM 7162

<400> SEQUENCE: 3
atgtctaaag tagtgtatgt gtcacatgat ggaacgcgtc gcgaactgga tgtggcggat      60
ggcgtcagcc tgatgcaggc tgcagtctcc aatggtatct acgatattgt cggtgattgt     120
ggcggcagcg ccagctgtgc cacctgccat gtctatgtga acgaagcgtt cacggacaag     180
gtgcccgccg ccaacgagcg ggaaatcggc atgctggagt gcgtcacggc cgaactgaag     240
ccgaacagca ggctctgctg ccagatcatc atgacgcccg agctggatgg catcgtggtc     300
gatgttcccg ataggcaatg gtaa                                            324

<210> SEQ ID NO 4
<211> LENGTH: 107
<212> TYPE: PRT
<213> ORGANISM: Pseudomonas putida
<220> FEATURE:
<221> NAME/KEY: misc_feature
<222> LOCATION: (1)..(107)
<223> OTHER INFORMATION: PpG786 strain DSM 7162
```

<400> SEQUENCE: 4

```
Met Ser Lys Val Val Tyr Val Ser His Asp Gly Thr Arg Arg Glu Leu
1               5                   10                  15

Asp Val Ala Asp Gly Val Ser Leu Met Gln Ala Ala Val Ser Asn Gly
            20                  25                  30

Ile Tyr Asp Ile Val Gly Asp Cys Gly Gly Ser Ala Ser Cys Ala Thr
        35                  40                  45

Cys His Val Tyr Val Asn Glu Ala Phe Thr Asp Lys Val Pro Ala Ala
    50                  55                  60

Asn Glu Arg Glu Ile Gly Met Leu Glu Cys Val Thr Ala Glu Leu Lys
65                  70                  75                  80

Pro Asn Ser Arg Leu Cys Cys Gln Ile Ile Met Thr Pro Glu Leu Asp
                85                  90                  95

Gly Ile Val Val Asp Val Pro Asp Arg Gln Trp
                100                 105
```

```
<210> SEQ ID NO 5
<211> LENGTH: 1248
<212> TYPE: DNA
<213> ORGANISM: Pseudomonas putida
<220> FEATURE:
<221> NAME/KEY: misc_feature
<222> LOCATION: (1)..(1248)
<223> OTHER INFORMATION: PpG786 strain DSM 7162
```

<400> SEQUENCE: 5

```
atgacgactg aaaccataca aagcaacgcc aatcttgccc ctctgccacc ccatgtgcca      60
gagcacctgg tattcgactt cgacatgtac aatccgtcga atctgtctgc cggcgtgcag     120
gaggcctggg cagttctgca agaatcaaac gtaccggatc tggtgtggac tcgctgcaac     180
ggcggacact ggatcgccac tcgcggccaa ctgatccgtg aggcctatga agattaccgc     240
cactttccca gcgagtgccc gttcatccct cgtgaagccg cgaagcctca cgacttcatt     300
cccacctcga tggatccgcc gagcagcgc cagtttcgtg cgctggccaa ccaagtggtt      360
ggcatgccgg tggtggataa gctggagaac cggatccagg agctggcctg ctcgctgatc     420
gagagcctgc gcccgcaagg acagtgcaac ttcaccgagg actacgccga cccttcccg      480 atacgcatct tcatgctgct cgcaggtcta ccggaagaag atatcccgca cttgaaatac     540
ctaacggatc agatgacccg tccggatggc agcatgacct tcgcagaggc caaggaggcg     600
ctctacgact atctgatacc gatcatcgag caacgcaggc agaagccggg aaccgacgct     660
atcagcatcg ttgccaacgg ccaggtcaat gggcgaccga tcaccagtga cgaagccaag     720
aggatgtgtg gcctgttact ggtcggcggc ctggatacgg tggtcaattt cctcagcttc     780
agcatggagt tcctggccaa aagcccggag catcgccagg agctgatcga gcgtcccgag     840
cgtattccag ccgcttgcga ggaactactc cggcgcttct cgctggttgc cgatggccgc     900
atcctcacct ccgattacga gtttcatggc gtgcaactga agaaaggtga ccagatcctg     960
ctaccgcaga tgctgtctgg cctggatgag cgcgaaaacg cctgcccgat gcacgtcgac    1020
ttcagtcgcc aaaaggtttc acacaccacc tttggccacg cagccatctg tgccttggc    1080 cagcacctgg cccgccggga atcatcgtc accctcaagg aatggctgac caggattcct    1140
gacttctcca ttgccccggg tgcccagatt cagcacaaga gcggcatcgt cagcggcgtg    1200
caggcactcc tctggtctg ggatccggcg actaccaaag cggtataa                 1248
```

```
<210> SEQ ID NO 6
<211> LENGTH: 415
<212> TYPE: PRT
<213> ORGANISM: Pseudomonas putida
<220> FEATURE:
<221> NAME/KEY: misc_feature
<222> LOCATION: (1)..(415)
<223> OTHER INFORMATION: PpG786 strain DSM 7162

<400> SEQUENCE: 6
```

Met Thr Thr Glu Thr Ile Gln Ser Asn Ala Asn Leu Ala Pro Leu Pro
1               5                   10                  15

Pro His Val Pro Glu His Leu Val Phe Asp Phe Asp Met Tyr Asn Pro
                20                  25                  30

Ser Asn Leu Ser Ala Gly Val Gln Glu Ala Trp Ala Val Leu Gln Glu
            35                  40                  45

Ser Asn Val Pro Asp Leu Val Trp Thr Arg Cys Asn Gly Gly His Trp
        50                  55                  60

Ile Ala Thr Arg Gly Gln Leu Ile Arg Glu Ala Tyr Glu Asp Tyr Arg
65                  70                  75                  80

His Phe Ser Ser Glu Cys Pro Phe Ile Pro Arg Glu Ala Gly Glu Ala
                85                  90                  95

Tyr Asp Phe Ile Pro Thr Ser Met Asp Pro Pro Glu Gln Arg Gln Phe
            100                 105                 110

Arg Ala Leu Ala Asn Gln Val Val Gly Met Pro Val Val Asp Lys Leu
        115                 120                 125

Glu Asn Arg Ile Gln Glu Leu Ala Cys Ser Leu Ile Glu Ser Leu Arg
130                 135                 140

Pro Gln Gly Gln Cys Asn Phe Thr Glu Asp Tyr Ala Glu Pro Phe Pro
145                 150                 155                 160

Ile Arg Ile Phe Met Leu Leu Ala Gly Leu Pro Glu Glu Asp Ile Pro
                165                 170                 175

His Leu Lys Tyr Leu Thr Asp Gln Met Thr Arg Pro Asp Gly Ser Met
            180                 185                 190

Thr Phe Ala Glu Ala Lys Glu Ala Leu Tyr Asp Tyr Leu Ile Pro Ile
        195                 200                 205

Ile Glu Gln Arg Arg Gln Lys Pro Gly Thr Asp Ala Ile Ser Ile Val
210                 215                 220

Ala Asn Gly Gln Val Asn Gly Arg Pro Ile Thr Ser Asp Glu Ala Lys
225                 230                 235                 240

Arg Met Cys Gly Leu Leu Leu Val Gly Gly Leu Asp Thr Val Val Asn
                245                 250                 255

Phe Leu Ser Phe Ser Met Glu Phe Leu Ala Lys Ser Pro Glu His Arg
            260                 265                 270

Gln Glu Leu Ile Glu Arg Pro Glu Arg Ile Pro Ala Ala Cys Glu Glu
        275                 280                 285

Leu Leu Arg Arg Phe Ser Leu Val Ala Asp Gly Arg Ile Leu Thr Ser
290                 295                 300

Asp Tyr Glu Phe His Gly Val Gln Leu Lys Lys Gly Asp Gln Ile Leu
305                 310                 315                 320

Leu Pro Gln Met Leu Ser Gly Leu Asp Glu Arg Glu Asn Ala Cys Pro
                325                 330                 335

Met His Val Asp Phe Ser Arg Gln Lys Val Ser His Thr Thr Phe Gly
            340                 345                 350

His Gly Ser His Leu Cys Leu Gly Gln His Leu Ala Arg Arg Glu Ile
        355                 360                 365

```
Ile Val Thr Leu Lys Glu Trp Leu Thr Arg Ile Pro Asp Phe Ser Ile
    370                 375                 380

Ala Pro Gly Ala Gln Ile Gln His Lys Ser Gly Ile Val Ser Gly Val
385                 390                 395                 400

Gln Ala Leu Pro Leu Val Trp Asp Pro Ala Thr Thr Lys Ala Val
                405                 410                 415

<210> SEQ ID NO 7
<211> LENGTH: 3150
<212> TYPE: DNA
<213> ORGANISM: Bacillus megaterium
<220> FEATURE:
<221> NAME/KEY: misc_feature
<222> LOCATION: (1)..(3150)
<223> OTHER INFORMATION: ATCC 14581

<400> SEQUENCE: 7
```

| | | | | |
|---|---|---|---|---|
| atgacaatta | agaaatgcc | tcagccaaaa | acgtttggag | agcttaaaaa tttaccgtta | 60 |
| ttaaacacag | ataaaccggt | tcaagctttg | atgaaaattg | cggatgaatt aggagaaatc | 120 |
| tttaaattcg | aggcgcctgg | tcgtgtaacg | cgctacttat | caagtcagcg tctaattaaa | 180 |
| gaagcatgcg | atgaatcacg | ctttgataaa | aacttaagtc | aagcgcttaa atttgtacgt | 240 |
| gattttgcag | agacgggtt | atttacaagc | tggacgcatg | aaaaaaattg gaaaaaagcg | 300 |
| cataatatct | tacttccaag | cttcagtcag | caggcaatga | aaggctatca tgcgatgatg | 360 |
| gtcgatatcg | ccgtgcagct | tgttcaaaag | tgggagcgtc | taaatgcaga tgagcatatt | 420 |
| gaagtaccgg | aagacatgac | acgtttaacg | cttgatacaa | ttggtctttg cggctttaac | 480 |
| tatcgctta | acagctttta | ccgagatcag | cctcatccat | ttattacaag tatggtccgt | 540 |
| gcactggatg | aagcaatgaa | caagctgcag | cgagcaaatc | cagacgaccc agcttatgat | 600 |
| gaaaacaagc | gccagtttca | agaagatatc | aaggtgatga | acgacctagt agataaaatt | 660 |
| attgcagatc | gcaaagcaag | cggtgaacaa | agcgatgatt | tattaacgca tatgctaaac | 720 |
| ggaaaagatc | cagaaacggg | tgagccgctt | gatgacgaga | cattcgcta tcaaattatt | 780 |
| acattcttaa | ttgcgggaca | cgaaacaaca | agtggtcttt | tatcatttgc gctgtatttc | 840 |
| ttagtgaaaa | atccacatgt | attacaaaaa | gcagcagaag | aagcagcacg agttctagta | 900 |
| gatcctgttc | caagctacaa | acaagtcaaa | cagcttaaat | atgtcggcat ggtcttaaac | 960 |
| gaagcgctgc | gcttatggcc | aactgctcct | gcgttttccc | tatatgcaaa agaagatacg | 1020 |
| gtgcttggag | gagaatatcc | tttagaaaaa | ggcgacgaac | taatggttct gattcctcag | 1080 |
| cttcaccgtg | ataaaacaat | tgggggagac | gatgtggaag | agttccgtcc agagcgtttt | 1140 |
| gaaaatccaa | gtgcgattcc | gcagcatgcg | tttaaaccgt | ttggaaacgg tcagcgtgcg | 1200 |
| tgtatcggtc | agcagttcgc | tcttcatgaa | gcaacgctgg | tacttggtat gatgctaaaa | 1260 |
| cactttgact | tgaagatca | tacaaactac | gagctggata | ttaaagaaac tttaacgtta | 1320 |
| aaacctgaag | gctttgtggt | aaaagcaaaa | tcgaaaaaaa | ttccgcttgg cggtattcct | 1380 |
| tcacctagca | ctgaacagtc | tgctaaaaaa | gtacgcaaaa | aggcagaaaa cgctcataat | 1440 |
| acgccgctgc | ttgtgctata | cggttcaaat | atgggaacag | ctgaaggaac ggcgcgtgat | 1500 |
| ttagcagata | ttgcaatgag | caaaggattt | gcaccgcagg | tcgcaacgct tgattcacac | 1560 |
| gccggaaatc | ttccgcgcga | aggagctgta | ttaattgtaa | cggcgtctta taacggtcat | 1620 |
| ccgcctgata | acgcaaagca | atttgtcgac | tggttagacc | aagcgtctgc tgatgaagta | 1680 |
| aaaggcgttc | gctactccgt | atttggatgc | ggcgataaaa | actgggctac tacgtatcaa | 1740 |

```
aaagtgcctg cttttatcga tgaaacgctt gccgctaaag gggcagaaaa catcgctgac    1800
cgcggtgaag cagatgcaag cgacgacttt gaaggcacat atgaagaatg gcgtgaacat    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taagtagag    2340 cttgaagcct tgcttgaaaa gcaagcctac aaagaacaag tgctggcaaa acgtttaaca    2400
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct tgtgcaggc gcgcaaacag    2760 ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc cctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                     3150
```

<210> SEQ ID NO 8
<211> LENGTH: 1049
<212> TYPE: PRT
<213> ORGANISM: Bacillus megaterium
<220> FEATURE:
<221> NAME/KEY: misc_feature
<222> LOCATION: (1)..(1049)
<223> OTHER INFORMATION: ATCC 14581

<400> SEQUENCE: 8

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95
```

```
Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
```

```
                515                 520                 525
Ala Val Leu Ile Val Thr Ala Ser Tyr Asn Gly His Pro Pro Asp Asn
    530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
                580                 585                 590
Lys Gly Ala Glu Asn Ile Ala Asp Arg Gly Glu Ala Asp Ala Ser Asp
                595                 600                 605
Asp Phe Glu Gly Thr Tyr Glu Glu Trp Arg Glu His Met Trp Ser Asp
            610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
                660                 665                 670
Leu Gln Gln Pro Gly Ser Ala Arg Ser Thr Arg His Leu Glu Ile Glu
            675                 680                 685
Leu Pro Lys Glu Ala Ser Tyr Gln Gly Asp His Leu Gly Val Ile
        690                 695                 700
Pro Arg Asn Tyr Glu Gly Ile Val Asn Arg Val Thr Ala Arg Phe Gly
705                 710                 715                 720
Leu Asp Ala Ser Gln Gln Ile Arg Leu Glu Ala Glu Glu Lys Leu
                725                 730                 735
Ala His Leu Pro Leu Ala Lys Thr Val Ser Val Glu Glu Leu Leu Gln
                740                 745                 750
Tyr Val Glu Leu Gln Asp Pro Val Thr Arg Thr Gln Leu Arg Ala Met
            755                 760                 765
Ala Ala Lys Thr Val Cys Pro Pro His Lys Val Glu Leu Glu Ala Leu
        770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Lys Phe Ser
                805                 810                 815
Glu Phe Ile Ala Leu Leu Pro Ser Ile Arg Pro Arg Tyr Tyr Ser Ile
                820                 825                 830
Ser Ser Ser Pro Arg Val Asp Glu Lys Gln Ala Ser Ile Thr Val Ser
        835                 840                 845
Val Val Ser Gly Glu Ala Trp Ser Gly Tyr Gly Glu Tyr Lys Gly Ile
        850                 855                 860
Ala Ser Asn Tyr Leu Ala Glu Leu Gln Glu Gly Asp Thr Ile Thr Cys
865                 870                 875                 880
Phe Ile Ser Thr Pro Gln Ser Glu Phe Thr Leu Pro Lys Asp Pro Glu
                885                 890                 895
Thr Pro Leu Ile Met Val Gly Pro Gly Thr Gly Val Ala Pro Phe Arg
            900                 905                 910
Gly Phe Val Gln Ala Arg Lys Gln Leu Lys Glu Gln Gly Gln Ser Leu
        915                 920                 925
Gly Glu Ala His Leu Tyr Phe Gly Cys Arg Ser Pro His Glu Asp Tyr
    930                 935                 940
```

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
            965                 970                 975

Gln His Val Met Glu Gln Asp Gly Lys Lys Leu Ile Glu Leu Leu Asp
        980                 985                 990

Gln Gly Ala His Phe Tyr Ile Cys Gly Asp Gly Ser Gln Met Ala Pro
    995                 1000                1005

Ala Val Glu Ala Thr Leu Met Lys Ser Tyr Ala Asp Val His Gln Val
   1010                 1015                1020

Ser Glu Ala Asp Ala Arg Leu Trp Leu Gln Gln Leu Glu Glu Lys Gly
1025                 1030                 1035                1040

Arg Tyr Ala Lys Asp Val Trp Ala Gly
            1045

<210> SEQ ID NO 9
<211> LENGTH: 1476
<212> TYPE: DNA
<213> ORGANISM: Escherichia coli
<220> FEATURE:
<221> NAME/KEY: misc_feature
<222> LOCATION: (1)..(1476)
<223> OTHER INFORMATION: K12 (MG1655)

<400> SEQUENCE: 9
atggcggtaa cgcaaacagc ccaggcctgt gacctggtca tttttcggcgc gaaaggcgac    60 cttgcgcgtc gtaaattgct gccttccctg tatcaactgg aaaaagccgg tcagctcaac   120
ccggacaccc ggattatcgg cgtagggcgt gctgactggg ataaagcggc ataccaaa    180 gttgtccgcg aggcgctcga aactttcatg aaagaaacca ttgatgaagg tttatgggac   240
accctgagtg cacgtctgga ttttgtaat ctcgatgtca atgacactgc tgcattcagc   300
cgtctcggcg cgatgctgga tcaaaaaaat cgtatcacca ttaactactt tgccatgccg   360
cccagcactt ttggcgcaat ttgcaaaggg cttggcgagg caaaactgaa tgctaaaccg   420
gcacgcgtag tcatggagaa accgctgggg acgtcgctgg cgacctcgca ggaaatcaat   480
gatcaggttg gcgaatactt cgaggagtgc caggtttacc gtatcgacca ctatcttggt   540
aaagaaacgg tgctgaacct gttggcgctg cgttttgcta actccctgtt tgtgaataac   600
tgggacaatc gcaccattga tcatgttgag attaccgtgg cagaagaagt ggggatcgaa   660
gggcgctggg gctattttga taaagccggt cagatgcgcg acatgatcca gaaccacctg   720
ctgcaaattc tttgcatgat tgcgatgtct ccgccgtctg acctgagcgc agacagcatc   780
cgcgatgaaa aagtgaaagt actgaagtct ctgcgccgca tcgaccgctc caacgtacgc   840
gaaaaaaccg tacgcgggca atatactgcg ggcttcgccc agggcaaaaa agtgccggga   900
tatctggaag aagagggcgc gaacaagagc agcaatacag aaactttcgt ggcgatccgc   960
gtcgacattg ataactggcg ctgggccggt gtgccattct acctgcgtac tggtaaacgt  1020
ctgccgacca atgttctga gtcgtggtc tatttcaaa cacctgaact gaatctgttt  1080
aaagaatcgt ggcaggatct gccgcagaat aaactgacta ccgtctgca acctgatgaa  1140 ggcgtggata tccaggtact gaataaagtt cctggccttg accacaaaca taacctgcaa  1200
atcaccaagc tggatctgag ctattcagaa acctttaatc agacgcatct ggcggatgcc  1260
tatgaacgtt tgctgctgga aaccatgcgt ggtattcagg cactgtttgt acgtcgcgac  1320
gaagtggaag aagcctggaa atgggtagac tccattactg aggcgtgggc gatggacaat  1380

```
gatgcgccga aaccgtatca ggccggaacc tggggacccg ttgcctcggt ggcgatgatt    1440
acccgtgatg gtcgttcctg gaatgagttt gagtaa                              1476
```

<210> SEQ ID NO 10
<211> LENGTH: 491
<212> TYPE: PRT
<213> ORGANISM: Escherichia coli
<220> FEATURE:
<221> NAME/KEY: misc_feature
<222> LOCATION: (1)..(491)
<223> OTHER INFORMATION: K12 (MG1655)

<400> SEQUENCE: 10

Met Ala Val Thr Gln Thr Ala Gln Ala Cys Asp Leu Val Ile Phe Gly
1               5                   10                  15

Ala Lys Gly Asp Leu Ala Arg Arg Lys Leu Leu Pro Ser Leu Tyr Gln
            20                  25                  30

Leu Glu Lys Ala Gly Gln Leu Asn Pro Asp Thr Arg Ile Ile Gly Val
        35                  40                  45

Gly Arg Ala Asp Trp Asp Lys Ala Ala Tyr Thr Lys Val Val Arg Glu
    50                  55                  60

Ala Leu Glu Thr Phe Met Lys Glu Thr Ile Asp Glu Gly Leu Trp Asp
65                  70                  75                  80

Thr Leu Ser Ala Arg Leu Asp Phe Cys Asn Leu Asp Val Asn Asp Thr
                85                  90                  95

Ala Ala Phe Ser Arg Leu Gly Ala Met Leu Asp Gln Lys Asn Arg Ile
            100                 105                 110

Thr Ile Asn Tyr Phe Ala Met Pro Pro Ser Thr Phe Gly Ala Ile Cys
        115                 120                 125

Lys Gly Leu Gly Glu Ala Lys Leu Asn Ala Lys Pro Ala Arg Val Val
    130                 135                 140

Met Glu Lys Pro Leu Gly Thr Ser Leu Ala Thr Ser Gln Glu Ile Asn
145                 150                 155                 160

Asp Gln Val Gly Glu Tyr Phe Glu Glu Cys Gln Val Tyr Arg Ile Asp
                165                 170                 175

His Tyr Leu Gly Lys Glu Thr Val Leu Asn Leu Leu Ala Leu Arg Phe
            180                 185                 190

Ala Asn Ser Leu Phe Val Asn Asn Trp Asp Asn Arg Thr Ile Asp His
        195                 200                 205

Val Glu Ile Thr Val Ala Glu Glu Val Gly Ile Glu Gly Arg Trp Gly
    210                 215                 220

Tyr Phe Asp Lys Ala Gly Gln Met Arg Asp Met Ile Gln Asn His Leu
225                 230                 235                 240

Leu Gln Ile Leu Cys Met Ile Ala Met Ser Pro Pro Ser Asp Leu Ser
                245                 250                 255

Ala Asp Ser Ile Arg Asp Glu Lys Val Lys Val Leu Lys Ser Leu Arg
            260                 265                 270

Arg Ile Asp Arg Ser Asn Val Arg Glu Lys Thr Val Arg Gly Gln Tyr
        275                 280                 285

Thr Ala Gly Phe Ala Gln Gly Lys Lys Val Pro Gly Tyr Leu Glu Glu
    290                 295                 300

Glu Gly Ala Asn Lys Ser Ser Asn Thr Glu Thr Phe Val Ala Ile Arg
305                 310                 315                 320

Val Asp Ile Asp Asn Trp Arg Trp Ala Gly Val Pro Phe Tyr Leu Arg
                325                 330                 335

```
Thr Gly Lys Arg Leu Pro Thr Lys Cys Ser Glu Val Val Tyr Phe
            340                 345                 350

Lys Thr Pro Glu Leu Asn Leu Phe Lys Glu Ser Trp Gln Asp Leu Pro
        355                 360                 365

Gln Asn Lys Leu Thr Ile Arg Leu Gln Pro Asp Glu Gly Val Asp Ile
    370                 375                 380

Gln Val Leu Asn Lys Val Pro Gly Leu Asp His Lys His Asn Leu Gln
385                 390                 395                 400

Ile Thr Lys Leu Asp Leu Ser Tyr Ser Glu Thr Phe Asn Gln Thr His
                405                 410                 415

Leu Ala Asp Ala Tyr Glu Arg Leu Leu Leu Glu Thr Met Arg Gly Ile
            420                 425                 430

Gln Ala Leu Phe Val Arg Arg Asp Glu Val Glu Glu Ala Trp Lys Trp
        435                 440                 445

Val Asp Ser Ile Thr Glu Ala Trp Ala Met Asp Asn Asp Ala Pro Lys
    450                 455                 460

Pro Tyr Gln Ala Gly Thr Trp Gly Pro Val Ala Ser Val Ala Met Ile
465                 470                 475                 480

Thr Arg Asp Gly Arg Ser Trp Asn Glu Phe Glu
                485                 490

<210> SEQ ID NO 11
<211> LENGTH: 37
<212> TYPE: DNA
<213> ORGANISM: Artificial Sequence
<220> FEATURE:
<223> OTHER INFORMATION: Synthetic Primer: camA_F

<400> SEQUENCE: 11
taagaaggag atatacatat gaacgcaaac gacaacg                             37

<210> SEQ ID NO 12
<211> LENGTH: 42
<212> TYPE: DNA
<213> ORGANISM: Artificial Sequence
<220> FEATURE:
<223> OTHER INFORMATION: Synthetic Primer: camA_R

<400> SEQUENCE: 12
catgaattct gtttcctgtg tgattaggca ctactcagtt ca                       42

<210> SEQ ID NO 13
<211> LENGTH: 42
<212> TYPE: DNA
<213> ORGANISM: Artificial Sequence
<220> FEATURE:
<223> OTHER INFORMATION: Synthetic Primer: camB_F

<400> SEQUENCE: 13
taatcacaca ggaaacagaa ttcatgtcta aagtagtgta tg                       42

<210> SEQ ID NO 14
<211> LENGTH: 40
<212> TYPE: DNA
<213> ORGANISM: Artificial Sequence
<220> FEATURE:
<223> OTHER INFORMATION: Synthetic Primer: camB_R

<400> SEQUENCE: 14
ggtttcttta ccagactcga ttaccattgc ctatcgggaa                          40
```

<210> SEQ ID NO 15
<211> LENGTH: 36
<212> TYPE: DNA
<213> ORGANISM: Artificial Sequence
<220> FEATURE:
<223> OTHER INFORMATION: Synthetic Primer: camC_F

<400> SEQUENCE: 15
aagaaggaga tataccatga cgactgaaac cataca                          36

<210> SEQ ID NO 16
<211> LENGTH: 40
<212> TYPE: DNA
<213> ORGANISM: Artificial Sequence
<220> FEATURE:
<223> OTHER INFORMATION: Synthetic Primer: camC_R

<400> SEQUENCE: 16
gcattatgcg gccgcaagct ttataccgct ttggtagtcg                      40

<210> SEQ ID NO 17
<211> LENGTH: 37
<212> TYPE: DNA
<213> ORGANISM: Artificial Sequence
<220> FEATURE:
<223> OTHER INFORMATION: Synthetic Primer: P450bm3_F

<400> SEQUENCE: 17
aagaaggaga tataccatga caattaaaga aatgcct                         37

<210> SEQ ID NO 18
<211> LENGTH: 40
<212> TYPE: DNA
<213> ORGANISM: Artificial Sequence
<220> FEATURE:
<223> OTHER INFORMATION: Synthetic Primer: P450bm3_R

<400> SEQUENCE: 18
gtggtggtgg tggtgctcga ttacccagcc cacacgtctt                      40

<210> SEQ ID NO 19
<211> LENGTH: 38
<212> TYPE: DNA
<213> ORGANISM: Artificial Sequence
<220> FEATURE:
<223> OTHER INFORMATION: Synthetic Primer: Zwf_F

<400> SEQUENCE: 19
ttaagaagga gatataccat ggcggtaacg caaacagc                        38

<210> SEQ ID NO 20
<211> LENGTH: 39
<212> TYPE: DNA
<213> ORGANISM: Artificial Sequence
<220> FEATURE:
<223> OTHER INFORMATION: Synthetic Primer: Zwf_R

<400> SEQUENCE: 20
tcgacctgca ggcgcgccgt tactcaaact cattccagg                       39

<210> SEQ ID NO 21
<211> LENGTH: 39
<212> TYPE: DNA
<213> ORGANISM: Artificial Sequence
<220> FEATURE:
<223> OTHER INFORMATION: Synthetic Forward primer for F351Y

```
<400> SEQUENCE: 21
aaggtttcac acaccaccta tggccacggc agccatctg                              39

<210> SEQ ID NO 22
<211> LENGTH: 39
<212> TYPE: DNA
<213> ORGANISM: Artificial Sequence
<220> FEATURE:
<223> OTHER INFORMATION: Synthetic Reverse primer for F351Y

<400> SEQUENCE: 22
cagatggctg ccgtggccat aggtggtgtg tgaaaccTt                              39

<210> SEQ ID NO 23
<211> LENGTH: 39
<212> TYPE: DNA
<213> ORGANISM: Artificial Sequence
<220> FEATURE:
<223> OTHER INFORMATION: Synthetic Forward primer for F351T

<400> SEQUENCE: 23
aaggtttcac acaccaccac cggccacggc agccatctg                              39

<210> SEQ ID NO 24
<211> LENGTH: 39
<212> TYPE: DNA
<213> ORGANISM: Artificial Sequence
<220> FEATURE:
<223> OTHER INFORMATION: Synthetic Reverse primer for F351T

<400> SEQUENCE: 24
cagatggctg ccgtggccgg tggtggtgtg tgaaaccTt                              39

<210> SEQ ID NO 25
<211> LENGTH: 39
<212> TYPE: DNA
<213> ORGANISM: Artificial Sequence
<220> FEATURE:
<223> OTHER INFORMATION: Synthetic Forward primer for F351N

<400> SEQUENCE: 25
aaggtttcac acaccaccaa cggccacggc agccatctg                              39

<210> SEQ ID NO 26
<211> LENGTH: 39
<212> TYPE: DNA
<213> ORGANISM: Artificial Sequence
<220> FEATURE:
<223> OTHER INFORMATION: Synthetic Reverse primer for F351N

<400> SEQUENCE: 26
cagatggctg ccgtggccgt tggtggtgtg tgaaaccTt                              39

<210> SEQ ID NO 27
<211> LENGTH: 39
<212> TYPE: DNA
<213> ORGANISM: Artificial Sequence
<220> FEATURE:
<223> OTHER INFORMATION: Synthetic Forward primer for F351Q

<400> SEQUENCE: 27
aaggtttcac acaccaccca gggccacggc agccatctg                              39

<210> SEQ ID NO 28
```

<210> SEQ ID NO 28
<211> LENGTH: 39
<212> TYPE: DNA
<213> ORGANISM: Artificial Sequence
<220> FEATURE:
<223> OTHER INFORMATION: Synthetic Reverse primer for F351Q

<400> SEQUENCE: 28
cagatggctg ccgtggccct gggtggtgtg tgaaaccttt                    39

<210> SEQ ID NO 29
<211> LENGTH: 39
<212> TYPE: DNA
<213> ORGANISM: Artificial Sequence
<220> FEATURE:
<223> OTHER INFORMATION: Synthetic Forward primer for F351H

<400> SEQUENCE: 29
aaggtttcac acaccaccca tggccacggc agccatctg                    39

<210> SEQ ID NO 30
<211> LENGTH: 39
<212> TYPE: DNA
<213> ORGANISM: Artificial Sequence
<220> FEATURE:
<223> OTHER INFORMATION: Synthetic Reverse primer for F351H

<400> SEQUENCE: 30
cagatggctg ccgtggccat gggtggtgtg tgaaaccttt                    39

<210> SEQ ID NO 31
<211> LENGTH: 39
<212> TYPE: DNA
<213> ORGANISM: Artificial Sequence
<220> FEATURE:
<223> OTHER INFORMATION: Synthetic Forward primer for F351D

<400> SEQUENCE: 31
aaggtttcac acaccaccga tggccacggc agccatctg                    39

<210> SEQ ID NO 32
<211> LENGTH: 39
<212> TYPE: DNA
<213> ORGANISM: Artificial Sequence
<220> FEATURE:
<223> OTHER INFORMATION: Synthetic Reverse primer for F351D

<400> SEQUENCE: 32
cagatggctg ccgtggccat cggtggtgtg tgaaaccttt                    39

<210> SEQ ID NO 33
<211> LENGTH: 39
<212> TYPE: DNA
<213> ORGANISM: Artificial Sequence
<220> FEATURE:
<223> OTHER INFORMATION: Synthetic Forward primer for N320W

<400> SEQUENCE: 33
tatgtcggca tggtcttatg ggaagcgctg cgcttatgg                    39

<210> SEQ ID NO 34
<211> LENGTH: 39
<212> TYPE: DNA
<213> ORGANISM: Artificial Sequence
<220> FEATURE:
<223> OTHER INFORMATION: Synthetic Reverse primer for N320W

<400> SEQUENCE: 34
ccataagcgc agcgcttccc ataagaccat gccgacata          39

<210> SEQ ID NO 35
<211> LENGTH: 39
<212> TYPE: DNA
<213> ORGANISM: Artificial Sequence
<220> FEATURE:
<223> OTHER INFORMATION: Forward primer for N320F

<400> SEQUENCE: 35
tatgtcggca tggtcttatt tgaagcgctg cgcttatgg          39

<210> SEQ ID NO 36
<211> LENGTH: 39
<212> TYPE: DNA
<213> ORGANISM: Artificial Sequence
<220> FEATURE:
<223> OTHER INFORMATION: Synthetic Reverse primer for N320F

<400> SEQUENCE: 36
ccataagcgc agcgcttcaa ataagaccat gccgacata          39

<210> SEQ ID NO 37
<211> LENGTH: 39
<212> TYPE: DNA
<213> ORGANISM: Artificial Sequence
<220> FEATURE:
<223> OTHER INFORMATION: Synthetic Forward primer for N320G

<400> SEQUENCE: 37
tatgtcggca tggtcttagg cgaagcgctg cgcttatgg          39

<210> SEQ ID NO 38
<211> LENGTH: 39
<212> TYPE: DNA
<213> ORGANISM: Artificial Sequence
<220> FEATURE:
<223> OTHER INFORMATION: Synthetic Reverse primer for N320G

<400> SEQUENCE: 38
ccataagcgc agcgcttcgc ctaagaccat gccgacata          39

<210> SEQ ID NO 39
<211> LENGTH: 39
<212> TYPE: DNA
<213> ORGANISM: Artificial Sequence
<220> FEATURE:
<223> OTHER INFORMATION: Synthetic Forward primer for N320P

<400> SEQUENCE: 39
tatgtcggca tggtcttacc ggaagcgctg cgcttatgg          39

<210> SEQ ID NO 40
<211> LENGTH: 39
<212> TYPE: DNA
<213> ORGANISM: Artificial Sequence
<220> FEATURE:
<223> OTHER INFORMATION: Synthetic Reverse primer for N320P

<400> SEQUENCE: 40
ccataagcgc agcgcttccg gtaagaccat gccgacata          39

<210> SEQ ID NO 41
<211> LENGTH: 39
<212> TYPE: DNA

```
<213> ORGANISM: Artificial Sequence
<220> FEATURE:
<223> OTHER INFORMATION: Synthetic Forward primer for N320S

<400> SEQUENCE: 41
tatgtcggca tggtcttaag cgaagcgctg cgcttatgg                           39

<210> SEQ ID NO 42
<211> LENGTH: 39
<212> TYPE: DNA
<213> ORGANISM: Artificial Sequence
<220> FEATURE:
<223> OTHER INFORMATION: Synthetic Reverse primer for N320S

<400> SEQUENCE: 42
ccataagcgc agcgcttcgc ttaagaccat gccgacata                           39

<210> SEQ ID NO 43
<211> LENGTH: 39
<212> TYPE: DNA
<213> ORGANISM: Artificial Sequence
<220> FEATURE:
<223> OTHER INFORMATION: Synthetic Forward primer for N320E

<400> SEQUENCE: 43
tatgtcggca tggtcttaga agaagcgctg cgcttatgg                           39

<210> SEQ ID NO 44
<211> LENGTH: 39
<212> TYPE: DNA
<213> ORGANISM: Artificial Sequence
<220> FEATURE:
<223> OTHER INFORMATION: Synthetic Reverse primer for N320E

<400> SEQUENCE: 44
ccataagcgc agcgcttctt ctaagaccat gccgacata                           39

<210> SEQ ID NO 45
<211> LENGTH: 3150
<212> TYPE: DNA
<213> ORGANISM: Artificial Sequence
<220> FEATURE:
<223> OTHER INFORMATION: Synthetic P450BM3 N320W gene

<400> SEQUENCE: 45
atgacaatta aagaaatgcc tcagccaaaa acgtttggag agcttaaaaa tttaccgtta    60
ttaaacacag ataaaccggt tcaagctttg atgaaaattg cggatgaatt aggagaaatc   120
tttaaattcg aggcgcctgg tcgtgtaacg cgctacttat caagtcagcg tctaattaaa   180
gaagcatgcg atgaatcacg ctttgataaa aacttaagtc aagcgcttaa atttgtacgt   240
gattttgcag gagacgggtt atttacaagc tggacgcatg aaaaaaattg gaaaaaagcg   300
cataatatct tacttccaag cttcagtcag caggcaatga aaggctatca tgcgatgatg   360
gtcgatatcg ccgtgcagct tgttcaaaag tgggagcgtc taaatgcaga tgagcatatt   420
gaagtaccgg aagacatgac acgtttaacg cttgatacaa ttggtctttg cggctttaac   480
tatcgcttta acagctttta ccgagatcag cctcatccat ttattacaag tatggtccgt   540
gcactggatg aagcaatgaa caagctgcag cgagcaaatc cagacgaccc agcttatgat   600
gaaaacaagc gccagtttca agaagatatc aaggtgatga acgacctagt agataaaatt   660
attgcagatc gcaaagcaag cggtgaacaa agcgatgatt tattaacgca tatgctaaac   720
ggaaaagatc cagaaacggg tgagccgctt gatgacgaga acattcgcta tcaaattatt   780
```

```
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttatgg    960
gaagcgctgc gcttatggcc aactgctcct gcgttttccc tatatgcaaa agaagatacg   1020
gtgcttggag gagaatatcc tttagaaaaa ggcgacgaac taatggttct gattcctcag   1080
cttcaccgtg ataaaacaat tggggagac gatgtgaag agttccgtcc agagcgtttt    1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctggata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg ctttttatcga tgaaacgctt gccgctaaag gggcagaaaa catcgctgac   1800
cgcggtgaag cagatgcaag cgacgacttt gaaggcacat atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taaagtagag   2340
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580 tataaggaa ttgcgtcgaa ctatcttgcc gagctgcaag aaggagatac gattacgtgc    2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg cttttctcg catgccaaat cagccgaaaa catacgttca gcacgtaatg   2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
```
cgatacgcaa aagacgtgtg ggctgggtaa                               3150

<210> SEQ ID NO 46
<211> LENGTH: 3150
<212> TYPE: DNA
<213> ORGANISM: Artificial Sequence
<220> FEATURE:
<223> OTHER INFORMATION: Synthetic P450BM3 N320F gene

<400> SEQUENCE: 46

| | |
|---|---:|
| atgacaatta aagaaatgcc tcagccaaaa acgtttggag agcttaaaaa tttaccgtta | 60 |
| ttaaacacag ataaaccggt tcaagctttg atgaaaattg cggatgaatt aggagaaatc | 120 |
| tttaaattcg aggcgcctgg tcgtgtaacg cgctacttat caagtcagcg tctaattaaa | 180 |
| gaagcatgcg atgaatcacg ctttgataaa aacttaagtc aagcgcttaa atttgtacgt | 240 |
| gattttgcag agacgggtt atttacaagc tggacgcatg aaaaaaattg gaaaaaagcg | 300 |
| cataatatct tacttccaag cttcagtcag caggcaatga aaggctatca tgcgatgatg | 360 |
| gtcgatatcg ccgtgcagct tgttcaaaag tgggagcgtc taaatgcaga tgagcatatt | 420 |
| gaagtaccgg aagacatgac acgtttaacg cttgatacaa ttggtctttg cggctttaac | 480 |
| tatcgcttta cagctttta ccgagatcag cctcatccat ttattacaag tatggtccgt | 540 |
| gcactggatg aagcaatgaa caagctgcag cgagcaaatc cagacgaccc agcttatgat | 600 |
| gaaaacaagc gccagtttca gaagatatc aaggtgatga cgacctagt agataaaatt | 660 |
| attgcagatc gcaaagcaag cggtgaacaa agcgatgatt tattaacgca tatgctaaac | 720 |
| ggaaaagatc cagaaacggg tgagccgctt gatgacgaga cattcgcta tcaaattatt | 780 |
| acattcttaa ttgcgggaca cgaaacaaca agtggtcttt tatcatttgc gctgtatttc | 840 |
| ttagtgaaaa atccacatgt attacaaaaa gcagcagaag aagcagcacg agttctagta | 900 |
| gatcctgttc aagctacaa acaagtcaaa cagcttaaat atgtcggcat ggtcttattt | 960 |
| gaagcgctgc gcttatggcc aactgctcct gcgttttccc tatatgcaaa agaagatacg | 1020 |
| gtgcttggag agaatatcc tttagaaaaa ggcgacgaac taatggttct gattcctcag | 1080 |
| cttcaccgtg ataaacaat tggggagac gatgtggaag agttccgtcc agagcgtttt | 1140 |
| gaaaatccaa gtgcgattcc gcagcatgcg tttaaaccgt ttggaaacgg tcagcgtgcg | 1200 |
| tgtatcggtc agcagttcgc tcttcatgaa gcaacgctgg tacttggtat gatgctaaaa | 1260 |
| cactttgact ttgaagatca tacaaactac gagctggata ttaagaaac tttaacgtta | 1320 |
| aaacctgaag ctttgtggt aaaagcaaaa tcgaaaaaaa ttccgcttgg cggtattcct | 1380 |
| tcacctagca ctgaacagtc tgctaaaaaa gtacgcaaaa aggcagaaaa cgctcataat | 1440 |
| acgccgctgc ttgtgctata cggttcaaat atgggaacag ctgaaggaac ggcgcgtgat | 1500 |
| ttagcagata ttgcaatgag caaaggattt gcaccgcagg tcgcaacgct tgattcacac | 1560 |
| gccggaaatc ttccgcgcga aggagctgta ttaattgtaa cggcgtctta taacggtcat | 1620 |
| ccgcctgata acgcaaagca atttgtcgac tggttagacc aagcgtctgc tgatgaagta | 1680 |
| aaaggcgttc gctactccgt atttggatgc ggcgataaaa actgggctac tacgtatcaa | 1740 |
| aaagtgcctg cttttatcga tgaaacgctt gccgctaaag gggcagaaaa catcgctgac | 1800 |
| cgcggtgaag cagatgcaag cgacgacttt gaaggcacat atgaagaatg cgtgaacat | 1860 |
| atgtggagtg acgtagcagc ctactttaac ctcgacattg aaaacagtga agataataaa | 1920 |
| tctactcttt cacttcaatt tgtcgacagc gccgcggata tgccgcttgc gaaaatgcac | 1980 |
| ggtgcgtttt caacgaacgt cgtagcaagc aaagaacttc aacagccagg cagtgcacga | 2040 |

```
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taaagtagag    2340
cttgaagcct tgcttgaaaa gcaagcctac aagaacaag tgctggcaaa acgtttaaca    2400
atgcttgaac tgcttgaaaa ataccccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg caagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                     3150
```

<210> SEQ ID NO 47
<211> LENGTH: 3150
<212> TYPE: DNA
<213> ORGANISM: Artificial Sequence
<220> FEATURE:
<223> OTHER INFORMATION: Synthetic P450BM3 N320G

<400> SEQUENCE: 47

```
atgacaatta aagaaatgcc tcagccaaaa acgtttggag agcttaaaaa tttaccgtta      60
ttaaacacag ataaaccggt tcaagctttg atgaaaattg cggatgaatt aggagaaatc     120
tttaaattcg aggcgcctgg tcgtgtaacg cgctacttat caagtcagcg tctaattaaa     180
gaagcatgcg atgaatcacg ctttgataaa aacttaagtc aagcgcttaa atttgtacgt     240
gattttgcag gagacgggtt atttacaagc tggacgcatg aaaaaaattg gaaaaaagcg     300
catatatatct tacttccaag cttcagtcag caggcaatga aaggctatca tgcgatgatg     360
gtcgatatcg ccgtgcagct tgttcaaaag tgggagcgtc taaatgcaga tgagcatatt     420
gaagtaccgg aagacatgac acgtttaacg cttgatacaa ttggtctttg cggctttaac     480
tatcgcttta caagctttta ccgagatcag cctcatccat ttattacaag tatggtccgt     540
gcactggatg aagcaatgaa caagctgcag cgagcaaatc cagacgaccc agcttatgat     600
gaaaacaagc gccagtttca agaagatatc aaggtgatga acgacctagt agataaaatt     660
attgcagatc gcaaagcaag cggtgaacaa agcgatgatt tattaacgca tatgctaaac     720
ggaaaagatc cagaaacggg tgagccgctt gatgacgaga acattcgcta tcaaattatt     780
acattcttaa ttgcgggaca cgaaacaaca agtggtcttt tatcatttgc gctgtatttc     840
ttagtgaaaa atccacatgt attacaaaaa gcagcagaag aagcagcacg agttctagta     900
```

```
gatcctgttc caagctacaa acaagtcaaa cagcttaaat atgtcggcat ggtcttaggc    960
gaagcgctgc gcttatggcc aactgctcct gcgttttccc tatatgcaaa agaagatacg   1020
gtgcttggag gagaatatcc tttagaaaaa ggcgacgaac taatggttct gattcctcag   1080
cttcaccgtg ataaaacaat ttggggagac gatgtggaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctggata ttaagaaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg ctttttatcga tgaaacgctt gccgctaaag gggcagaaaa catcgctgac   1800
cgcggtgaag cagatgcaag cgacgacttt gaaggcacat atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taagtagag    2340
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct tgtgtcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg ctttttctcg catgccaaat cagccgaaaa catacgttca gcacgtaatg   2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg ggctgggtaa                                    3150
```

<210> SEQ ID NO 48
<211> LENGTH: 3150

<212> TYPE: DNA
<213> ORGANISM: Artificial Sequence
<220> FEATURE:
<223> OTHER INFORMATION: Synthetic P450BM3 N320P

<400> SEQUENCE: 48

| | |
|---|---:|
| atgacaatta aagaaatgcc tcagccaaaa acgtttggag agcttaaaaa tttaccgtta | 60 |
| ttaaacacag ataaaccggt tcaagctttg atgaaaattg cggatgaatt aggagaaatc | 120 |
| tttaaattcg aggcgcctgg tcgtgtaacg cgctacttat caagtcagcg tctaattaaa | 180 |
| gaagcatgcg atgaatcacg ctttgataaa aacttaagtc aagcgcttaa atttgtacgt | 240 |
| gatttttgcag gagacgggtt atttacaagc tggacgcatg aaaaaaattg gaaaaaagcg | 300 |
| cataatatct tacttccaag cttcagtcag caggcaatga aaggctatca tgcgatgatg | 360 |
| gtcgatatcg ccgtgcagct tgttcaaaag tgggagcgtc taaatgcaga tgagcatatt | 420 |
| gaagtaccgg aagacatgac acgtttaacg cttgatacaa ttggtctttg cggctttaac | 480 |
| tatcgcttta acagctttta ccgagatcag cctcatccat ttattacaag tatggtccgt | 540 |
| gcactggatg aagcaatgaa caagctgcag cgagcaaatc cagacgaccc agcttatgat | 600 |
| gaaaacaagc gccagtttca agaagatatc aaggtgatga cgacctagt agataaaatt | 660 |
| attgcagatc gcaaagcaag cggtgaacaa agcgatgatt tattaacgca tatgctaaac | 720 |
| ggaaaagatc cagaaacggg tgagccgctt gatgacgaga acattcgcta tcaaattatt | 780 |
| acattcttaa ttgcgggaca cgaaacaaca agtggtcttt atcatttgc gctgtatttc | 840 |
| ttagtgaaaa atccacatgt attacaaaaa gcagcagaag aagcagcacg agttctagta | 900 |
| gatcctgttc caagctacaa acaagtcaaa cagcttaaat atgtcggcat ggtcttaccg | 960 |
| gaagcgctgc gcttatggcc aactgctcct gcgttttccc tatatgcaaa agaagatacg | 1020 |
| gtgcttggag gagaatatcc tttagaaaaa ggcgacgaac taatggttct gattcctcag | 1080 |
| cttcaccgtg ataaaacaat tggggagac gatgtggaag agttccgtcc agagcgtttt | 1140 |
| gaaaatccaa gtgcgattcc gcagcatgcg tttaaaccgt ttggaacgg tcagcgtgcg | 1200 |
| tgtatcggtc agcagttcgc tcttcatgaa gcaacgctgg tacttggtat gatgctaaaa | 1260 |
| cactttgact ttgaagatca tacaaactac gagctggata ttaaagaaac tttaacgtta | 1320 |
| aaacctgaag ctttgtggt aaaagcaaaa tcgaaaaaaa ttccgcttgg cggtattcct | 1380 |
| tcacctagca ctgaacagtc tgctaaaaaa gtacgcaaaa aggcagaaaa cgctcataat | 1440 |
| acgccgctgc ttgtgctata cggttcaaat atgggaacag ctgaaggaac ggcgcgtgat | 1500 |
| ttagcagata ttgcaatgag caaaggattt gcaccgcagg tcgcaacgct tgattcacac | 1560 |
| gccggaaatc ttccgcgcga aggagctgta ttaattgtaa cggcgtctta taacggtcat | 1620 |
| ccgcctgata acgcaaagca atttgtcgac tggttagacc aagcgtctgc tgatgaagta | 1680 |
| aaaggcgttc gctactccgt atttggatgc ggcgataaaa actgggctac tacgtatcaa | 1740 |
| aaagtgcctg ctttatcga tgaaacgctt gccgctaaag ggcagaaaaa catcgctgac | 1800 |
| cgcggtgaag cagatgcaag cgacgacttt gaaggcacat atgaagaatg cgtgaacat | 1860 |
| atgtggagtg acgtagcagc ctactttaac ctcgacattg aaaacagtga agataataaa | 1920 |
| tctactcttt cacttcaatt tgtcgacagc gccgcgata tgccgcttgc gaaaatgcac | 1980 |
| ggtgcgtttt caacgaacgt cgtagcaagc aaagaacttc aacagccagg cagtgcacga | 2040 |
| agcacgcgac atcttgaaat tgaacttcca aagaagctt cttatcaaga aggagatcat | 2100 |
| ttaggtgtta ttcctcgcaa ctatgaagga atagtaaacc gtgtaacagc aaggttcggc | 2160 |

| | |
|---|---|
| ctagatgcat cacagcaaat ccgtctggaa gcagaagaag aaaaattagc tcatttgcca | 2220 |
| ctcgctaaaa cagtatccgt agaagagctt ctgcaatacg tggagcttca agatcctgtt | 2280 |
| acgcgcacgc agcttcgcgc aatggctgct aaaacggtct gcccgccgca taaagtagag | 2340 |
| cttgaagcct tgcttgaaaa gcaagcctac aaagaacaag tgctggcaaa acgtttaaca | 2400 |
| atgcttgaac tgcttgaaaa atacccggcg tgtgaaatga aattcagcga atttatcgcc | 2460 |
| cttctgccaa gcatacgccc gcgctattac tcgatttctt catcacctcg tgtcgatgaa | 2520 |
| aaacaagcaa gcatcacggt cagcgttgtc tcaggagaag cgtggagcgg atatggagaa | 2580 |
| tataaaggaa ttgcgtcgaa ctatcttgcc gagctgcaag aaggagatac gattacgtgc | 2640 |
| tttatttcca caccgcagtc agaatttacg ctgccaaaag accctgaaac gccgcttatc | 2700 |
| atggtcggac cgggaacagg cgtcgcgccg tttagaggct ttgtgcaggc gcgcaaacag | 2760 |
| ctaaaagaac aaggacagtc acttggagaa gcacatttat acttcggctg ccgttcacct | 2820 |
| catgaagact atctgtatca agaagagctt gaaaacgccc aaagcgaagg catcattacg | 2880 |
| cttcataccg ctttttctcg catgccaaat cagccgaaaa catacgttca gcacgtaatg | 2940 |
| gaacaagacg gcaagaaatt gattgaactt cttgatcaag gagcgcactt ctatatttgc | 3000 |
| ggagacggaa gccaaatggc acctgccgtt gaagcaacgc ttatgaaaag ctatgctgac | 3060 |
| gttcaccaag tgagtgaagc agacgctcgc ttatggctgc agcagctaga gaaaaaggc | 3120 |
| cgatacgcaa aagacgtgtg ggctgggtaa | 3150 |

<210> SEQ ID NO 49
<211> LENGTH: 3150
<212> TYPE: DNA
<213> ORGANISM: Artificial Sequence
<220> FEATURE:
<223> OTHER INFORMATION: Synthetic P450BM3 N320S

<400> SEQUENCE: 49

| | |
|---|---|
| atgacaatta aagaaatgcc tcagccaaaa acgtttggag agcttaaaaa tttaccgtta | 60 |
| ttaaacacag ataaaccggt tcaagctttg atgaaaattg cggatgaatt aggagaaatc | 120 |
| tttaaattcg aggcgcctgg tcgtgtaacg cgctacttat caagtcagcg tctaattaaa | 180 |
| gaagcatgcg atgaatcacg cttgataaa aacttaagtc aagcgcttaa atttgtacgt | 240 |
| gattttgcag gagacgggtt atttacaagc tggacgcatg aaaaaaattg gaaaaaagcg | 300 |
| cataatatct tacttccaag cttcagtcag caggcaatga aaggctatca tgcgatgatg | 360 |
| gtcgatatcg ccgtgcagct tgttcaaaag tgggagcgtc taaatgcaga tgagcatatt | 420 |
| gaagtaccgg aagacatgac acgtttaacg cttgatacaa ttggtctttg cggctttaac | 480 |
| tatcgcttta acagctttta ccgagatcag cctcatccat ttattacaag tatggtccgt | 540 |
| gcactggatg aagcaatgaa caagctgcag cgagcaaatc cagacgaccc agcttatgat | 600 |
| gaaaacaagc gccagtttca gaagatatc aaggtgatga cgacctagt agataaaatt | 660 |
| attgcagatc gcaaagcaag cggtgaacaa agcgatgatt tattaacgca tatgctaaac | 720 |
| ggaaaagatc cagaaacggg tgagccgctt gatgacgaga cattcgcta tcaaattatt | 780 |
| acattcttaa ttgcgggaca cgaaacaaca agtggtcttt atcatttgc gctgtatttc | 840 |
| ttagtgaaaa atccacatgt attacaaaaa gcagcagaag aagcagcacg agttctagta | 900 |
| gatcctgttc caagctacaa acaagtcaaa cagcttaaat atgtcggcat ggtcttaagc | 960 |
| gaagcgctgc gcttatggcc aactgctcct gcgttttccc tatatgcaaa agaagatacg | 1020 |
| gtgcttggag gagaatatcc tttagaaaaa ggcgacgaac taatggttct gattcctcag | 1080 |

```
cttcaccgtg ataaaacaat ttggggagac gatgtggaag agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctggata ttaaagaaac tttaacgtta    1320
aaacctgaag gctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattccacac   1560 gccggaaatc ttccgcgcga aggagctgta ttaattgtaa cggcgtctta taacggtcat    1620
ccgcctgata cgcaaagca atttgtcgac tggttagacc aagcgtctgc tgatgaagta     1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg cgtgaacat    1860 atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taagtagag    2340 cttgaagcct tgcttgaaaa gcaagcctac aaagaacaag tgctggcaaa cgtttaaca    2400 atgcttgaac tgcttgaaaa atacccggcg tgtgaaatga aattcagcga atttatcgcc    2460
cttctgccaa gcatacgccc cgcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct tgtgcaggc gcgcaaacag    2760 ctaaaagaac aaggacagtc acttggagaa gcacattat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                     3150
```

<210> SEQ ID NO 50  
<211> LENGTH: 3150  
<212> TYPE: DNA  
<213> ORGANISM: Artificial Sequence  
<220> FEATURE:  
<223> OTHER INFORMATION: Synthetic P450BM3 N320E

<400> SEQUENCE: 50

```
atgacaatta aagaaatgcc tcagccaaaa acgtttggag agcttaaaaa tttaccgtta      60
ttaaacacag ataaaccggt tcaagctttg atgaaaattg cggatgaatt aggagaaatc     120
tttaaattcg aggcgcctgg tcgtgtaacg cgctacttat caagtcagcg tctaattaaa     180
gaagcatgcg atgaatcacg ctttgataaa aacttaagtc aagcgcttaa atttgtacgt     240
gattttgcag gagacgggtt atttacaagc tggacgcatg aaaaaaattg gaaaaaagcg     300
cataatatct tacttccaag cttcagtcag caggcaatga aaggctatca tgcgatgatg     360
gtcgatatcg ccgtgcagct tgttcaaaag tgggagcgtc taaatgcaga tgagcatatt     420
gaagtaccgg aagacatgac acgtttaacg cttgatacaa ttggtctttg cggctttaac     480
tatcgcttta acagctttta ccgagatcag cctcatccat ttattacaag tatggtccgt     540
gcactggatg aagcaatgaa caagctgcag cgagcaaatc cagacgaccc agcttatgat     600
gaaaacaagc gccagtttca agaagatatc aaggtgatga cgacctagt agataaaatt      660
attgcagatc gcaaagcaag cggtgaacaa agcgatgatt tattaacgca tatgctaaac     720
ggaaaagatc cagaaacggg tgagccgctt gatgacgaga acattcgcta tcaaattatt     780
acattcttaa ttgcgggaca cgaaacaaca agtggtcttt tatcatttgc gctgtatttc     840
ttagtgaaaa atccacatgt attacaaaaa gcagcagaag aagcagcacg agttctagta     900
gatcctgttc aagctacaa acaagtcaaa cagcttaaat atgtcggcat ggtcttagaa      960
gaagcgctgc gcttatggcc aactgctcct gcgttttccc tatatgcaaa agaagatacg    1020
gtgcttggag gagaatatcc tttagaaaaa ggcgacgaac taatggttct gattcctcag    1080
cttcaccgtg ataaaacaat tgggggagac gatgtggaag agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact tgaagatca tacaaactac gagctggata ttaaagaaac tttaacgtta     1320
aaacctgaag gctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt ccgctaaag gggcagaaaa catcgctgac    1800
cgcggtgaag cagatgcaag cgacgacttt gaaggcacat atgaagaatg cgtgaacat    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taaagtagag    2340
```

```
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct tgtgcaggc gcgcaaacag    2760 ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg ctttttctcg catgccaaat cagccgaaaa catacgttca gcacgtaatg   2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaggc   3120 cgatacgcaa aagacgtgtg ggctgggtaa                                   3150

<210> SEQ ID NO 51
<211> LENGTH: 1248
<212> TYPE: DNA
<213> ORGANISM: Artificial Sequence
<220> FEATURE:
<223> OTHER INFORMATION: Synthetic CamC F351Y

<400> SEQUENCE: 51
atgacgactg aaaccataca aagcaacgcc aatcttgccc ctctgccacc ccatgtgcca     60
gagcacctgg tattcgactt cgacatgtac aatccgtcga atctgtctgc cggcgtgcag    120
gaggcctggg cagttctgca agaatcaaac gtaccggatc tggtgtggac tcgctgcaac    180
ggcggacact ggatcgccac tcgcggccaa ctgatccgtg aggcctatga agattaccgc    240
cacttttcca gcgagtgccc cgttcatccc cgtgaagccg gcgaagccta cgacttcatt    300
cccacctcga tggatccgcc cgagcagcgc cagtttcgtg cgctggccaa ccaagtggtt    360
ggcatgccgg tggtggataa gctggagaac cggatccagg agctggcctg ctcgctgatc   420
gagagcctgc gcccgcaagg acagtgcaac ttcaccgagg actacgccga acccttcccg   480
atacgcatct tcatgctgct cgcaggtcta ccggaagaag atatcccgca cttgaaatac   540
ctaacggatc agatgacccg tccggatggc agcatgacct tcgcagaggc caaggaggcg   600
ctctacgact atctgatacc gatcatcgag caacgcaggc agaagccggg aaccgacgct   660
atcagcatcg ttgccaacgg ccaggtcaat gggcgaccga tcaccagtga cgaagccaag   720
aggatgtgtg gcctgttact ggtcggcggc ctggatacgg tggtcaattt cctcagcttc   780
agcatggagt tcctggccaa agcccggag catcgccagg agctgatcga gcgtcccgag    840
cgtattccag ccgcttgcga ggaactactc cggcgcttct cgctggttgc cgatggccgc   900
atcctcacct ccgattacga gtttcatggc gtgcaactga gaaaggtga ccagatcctg    960 ctaccgcaga tgctgtctgg cctggatgag cgcgaaaacg cctgcccgat gcacgtcgac   1020
ttcagtcgcc aaaaggtttc acacaccacc tatggccacg cagccatct gtgccttggc    1080 cagcaccgg cccgccggga atcatcgtc accctcaagg aatggctgac caggattcct     1140
gacttctcca ttgccccggg tgcccagatt cagcacaaga gcggcatcgt cagcggcgtg   1200
```

```
caggcactcc ctctggtctg ggatccggcg actaccaaag cggtataa          1248
```

<210> SEQ ID NO 52
<211> LENGTH: 1248
<212> TYPE: DNA
<213> ORGANISM: Artificial Sequence
<220> FEATURE:
<223> OTHER INFORMATION: Synthetic CamC F351T

<400> SEQUENCE: 52

```
atgacgactg aaaccataca aagcaacgcc aatcttgccc ctctgccacc ccatgtgcca    60
gagcacctgg tattcgactt cgacatgtac aatccgtcga atctgtctgc cggcgtgcag   120
gaggcctggg cagttctgca agaatcaaac gtaccggatc tggtgtggac tcgctgcaac   180
ggcggacact ggatcgccac tcgcggccaa ctgatccgtg aggcctatga agattaccgc   240
cacttttcca gcgagtgccc gttcatccct cgtgaagccg gcgaagccta cgacttcatt   300
cccacctcga tggatccgcc cgagcagcgc cagtttcgtg cgctggccaa ccaagtggtt   360
ggcatgccgg tggtggataa gctggagaac cggatccagg agctggcctg ctcgctgatc   420
gagagcctgc gcccgcaagg acagtgcaac ttcaccgagg actacgccga acccttcccg   480
atacgcatct tcatgctgct cgcaggtcta ccggaagaag atatcccgca cttgaaatac   540
ctaacggatc agatgacccg tccggatggc agcatgacct tcgcagaggc caaggaggcg   600
ctctacgact atctgataccc gatcatcgag caacgcaggc agaagccggg aaccgacgct   660
atcagcatcg ttgccaacgg ccaggtcaat gggcgaccga tcaccagtga cgaagccaag   720
aggatgtgtg gcctgttact ggtcggcggc ctggatacgt ggtcaatttt cctcagcttc   780
agcatggagt tcctggccaa aagcccggag catcgccagg agctgatcga gcgtcccgag   840
cgtattccag ccgcttgcga ggaactactc cggcgcttct cgctggttgc cgatggccgc   900
atcctcacct ccgattacga gtttcatggc gtgcaactga gaaaggtga ccagatcctg   960
ctaccgcaga tgctgtctgg cctggatgag gcgaaaacg cctgcccgat gcacgtcgac  1020
ttcagtcgcc aaaaggtttc acacaccacc accggccacg gcagccatct gtgccttggc  1080
cagcacctgg cccgcgggga atcatcgtc accctcaagg aatggctgac caggattcct  1140
gacttctcca ttgccccggg tgcccagatt cagcacaaga gcggcatcgt cagcggcgtg  1200
caggcactcc ctctggtctg ggatccggcg actaccaaag cggtataa              1248
```

<210> SEQ ID NO 53
<211> LENGTH: 1248
<212> TYPE: DNA
<213> ORGANISM: Artificial Sequence
<220> FEATURE:
<223> OTHER INFORMATION: Synthetic CamC F351N

<400> SEQUENCE: 53

```
atgacgactg aaaccataca aagcaacgcc aatcttgccc ctctgccacc ccatgtgcca    60
gagcacctgg tattcgactt cgacatgtac aatccgtcga atctgtctgc cggcgtgcag   120
gaggcctggg cagttctgca agaatcaaac gtaccggatc tggtgtggac tcgctgcaac   180
ggcggacact ggatcgccac tcgcggccaa ctgatccgtg aggcctatga agattaccgc   240
cacttttcca gcgagtgccc gttcatccct cgtgaagccg gcgaagccta cgacttcatt   300
cccacctcga tggatccgcc cgagcagcgc cagtttcgtg cgctggccaa ccaagtggtt   360
ggcatgccgg tggtggataa gctggagaac cggatccagg agctggcctg ctcgctgatc   420
gagagcctgc gcccgcaagg acagtgcaac ttcaccgagg actacgccga acccttcccg   480
```

```
atacgcatct tcatgctgct cgcaggtcta ccggaagaag atatcccgca cttgaaatac        540
ctaacggatc agatgacccg tccggatggc agcatgacct tcgcagaggc caaggaggcg        600
ctctacgact atctgatacc gatcatcgag caacgcaggc agaagccggg aaccgacgct        660
atcagcatcg ttgccaacgg ccaggtcaat gggcgaccga tcaccagtga cgaagccaag        720
aggatgtgtg gcctgttact ggtcggcggc ctggatacgg tggtcaattt cctcagcttc        780
agcatggagt tcctggccaa aagcccggag catcgccagg agctgatcga gcgtcccgag        840
cgtattccag ccgcttgcga ggaactactc cggcgcttct cgctggttgc cgatggccgc        900
atcctcacct ccgattacga gtttcatggc gtgcaactga agaaaggtga ccagatcctg        960
ctaccgcaga tgctgtctgg cctggatgag cgcgaaaacg cctgcccgat gcacgtcgac       1020
ttcagtcgcc aaaaggtttc acacaccacc aacggccacg cagccatctg tgccttggc        1080 cagcacctgg cccgccggga atcatcgtc accctcaagg aatggctgac caggattcct       1140
gacttctcca ttgccccggg tgcccagatt cagcacaaga gcggcatcgt cagcggcgtg       1200
caggcactcc ctctggtctg ggatccggcg actaccaaag cggtataa                   1248
```

<210> SEQ ID NO 54
<211> LENGTH: 1248
<212> TYPE: DNA
<213> ORGANISM: Artificial Sequence
<220> FEATURE:
<223> OTHER INFORMATION: Synthetic CamC F351Q

<400> SEQUENCE: 54

```
atgacgactg aaaccataca aagcaacgcc aatcttgccc ctctgccacc ccatgtgcca         60
gagcacctgg tattcgactt cgacatgtac aatccgtcga atctgtctgc cggcgtgcag        120
gaggcctggg cagttctgca agaatcaaac gtaccggatc tggtgtggac tcgctgcaac        180
ggcggacact ggatcgccac tcgcggccaa ctgatccgtg aggcctatga agattaccgc        240
cacttttcca gcgagtgccc gttcatccct cgtgaagccg gcgaagccta cgacttcatt        300
cccacctcga tggatccgcc cgagcagcgc cagtttcgtg cgctggccaa ccaagtggtt        360
ggcatgccgg tggtggataa gctggagaac cggatccagg agctggcctg ctcgctgatc        420
gagagcctgc gcccgcaagg acagtgcaac ttcaccgagg actacgccga acccttcccg        480
atacgcatct tcatgctgct cgcaggtcta ccggaagaag atatcccgca cttgaaatac        540
ctaacggatc agatgacccg tccggatggc agcatgacct tcgcagaggc caaggaggcg        600
ctctacgact atctgatacc gatcatcgag caacgcaggc agaagccggg aaccgacgct        660
atcagcatcg ttgccaacgg ccaggtcaat gggcgaccga tcaccagtga cgaagccaag        720
aggatgtgtg gcctgttact ggtcggcggc ctggatacgg tggtcaattt cctcagcttc        780
agcatggagt tcctggccaa aagcccggag catcgccagg agctgatcga gcgtcccgag        840
cgtattccag ccgcttgcga ggaactactc cggcgcttct cgctggttgc cgatggccgc        900
atcctcacct ccgattacga gtttcatggc gtgcaactga agaaaggtga ccagatcctg        960
ctaccgcaga tgctgtctgg cctggatgag cgcgaaaacg cctgcccgat gcacgtcgac       1020
ttcagtcgcc aaaaggtttc acacaccacc cagggccacg cagccatctg tgccttggc        1080 cagcacctgg cccgccggga atcatcgtc accctcaagg aatggctgac caggattcct       1140
gacttctcca ttgccccggg tgcccagatt cagcacaaga gcggcatcgt cagcggcgtg       1200
caggcactcc ctctggtctg ggatccggcg actaccaaag cggtataa                   1248
```

<210> SEQ ID NO 55
<211> LENGTH: 1248
<212> TYPE: DNA
<213> ORGANISM: Artificial Sequence
<220> FEATURE:
<223> OTHER INFORMATION: Synthetic CamC F351H

<400> SEQUENCE: 55

| | | | | | |
|---|---|---|---|---|---|
| atgacgactg | aaaccataca | aagcaacgcc | aatcttgccc | ctctgccacc | ccatgtgcca | 60 |
| gagcacctgg | tattcgactt | cgacatgtac | aatccgtcga | atctgtctgc | cggcgtgcag | 120 |
| gaggcctggg | cagttctgca | agaatcaaac | gtaccggatc | tggtgtggac | tcgctgcaac | 180 |
| ggcggacact | ggatcgccac | tcgcggccaa | ctgatccgtg | aggcctatga | agattaccgc | 240 |
| cacttttcca | gcgagtgccc | gttcatccct | cgtgaagccg | gcgaagccta | cgacttcatt | 300 |
| cccacctcga | tggatccgcc | cgagcagcgc | cagtttcgtg | cgctggccaa | ccaagtggtt | 360 |
| ggcatgccgg | tggtggataa | gctggagaac | cggatccagg | agctggcctg | ctcgctgatc | 420 |
| gagagcctgc | gcccgcaagg | acagtgcaac | ttcaccgagg | actacgccga | acccttcccg | 480 |
| atacgcatct | tcatgctgct | cgcaggtcta | ccggaagaag | atatcccgca | cttgaaatac | 540 |
| ctaacggatc | agatgacccg | tccggatggc | agcatgacct | tcgcagaggc | caaggaggcg | 600 |
| ctctacgact | atctgatacc | gatcatcgag | caacgcaggc | agaagccggg | aaccgacgct | 660 |
| atcagcatcg | ttgccaacgg | ccaggtcaat | gggcgaccga | tcaccagtga | cgaagccaag | 720 |
| aggatgtgtg | gcctgttact | ggtcggcggc | ctggatacgg | tggtcaattt | cctcagcttc | 780 |
| agcatggagt | tcctggccaa | aagcccggag | catcgccagg | agctgatcga | gcgtcccgag | 840 |
| cgtattccag | ccgcttgcga | ggaactactc | cggcgcttct | cgctggttgc | cgatggccgc | 900 |
| atcctcacct | ccgattacga | gtttcatggc | gtgcaactga | agaaaggtga | ccagatcctg | 960 |
| ctaccgcaga | tgctgtctgg | cctggatgag | cgcgaaaacg | cctgcccgat | gcacgtcgac | 1020 |
| ttcagtcgcc | aaaaggtttc | acacaccacc | catggccacg | cagccatct | gtgccttggc | 1080 |
| cagcacctgg | cccgccggga | aatcatcgtc | accctcaagg | aatggctgac | caggattcct | 1140 |
| gacttctcca | ttgccccggg | tgcccagatt | cagcacaaga | gcggcatcgt | cagcggcgtg | 1200 |
| caggcactcc | ctctggtctg | ggatccggcg | actaccaaag | cggtataa | | 1248 |

<210> SEQ ID NO 56
<211> LENGTH: 1248
<212> TYPE: DNA
<213> ORGANISM: Artificial Sequence
<220> FEATURE:
<223> OTHER INFORMATION: Synthetic CamC F351D

<400> SEQUENCE: 56

| | | | | | |
|---|---|---|---|---|---|
| atgacgactg | aaaccataca | aagcaacgcc | aatcttgccc | ctctgccacc | ccatgtgcca | 60 |
| gagcacctgg | tattcgactt | cgacatgtac | aatccgtcga | atctgtctgc | cggcgtgcag | 120 |
| gaggcctggg | cagttctgca | agaatcaaac | gtaccggatc | tggtgtggac | tcgctgcaac | 180 |
| ggcggacact | ggatcgccac | tcgcggccaa | ctgatccgtg | aggcctatga | agattaccgc | 240 |
| cacttttcca | gcgagtgccc | gttcatccct | cgtgaagccg | gcgaagccta | cgacttcatt | 300 |
| cccacctcga | tggatccgcc | cgagcagcgc | cagtttcgtg | cgctggccaa | ccaagtggtt | 360 |
| ggcatgccgg | tggtggataa | gctggagaac | cggatccagg | agctggcctg | ctcgctgatc | 420 |
| gagagcctgc | gcccgcaagg | acagtgcaac | ttcaccgagg | actacgccga | acccttcccg | 480 |
| atacgcatct | tcatgctgct | cgcaggtcta | ccggaagaag | atatcccgca | cttgaaatac | 540 |

```
ctaacggatc agatgacccg tccggatggc agcatgacct tcgcagaggc caaggaggcg    600
ctctacgact atctgatacc gatcatcgag caacgcaggc agaagccggg aaccgacgct    660
atcagcatcg ttgccaacgg ccaggtcaat gggcgaccga tcaccagtga cgaagccaag    720
aggatgtgtg gcctgttact ggtcggcggc ctggatacga tggtcaattt cctcagcttc    780
agcatggagt tcctggccaa aagcccggag catcgccagg agctgatcga gcgtcccgag    840
cgtattccag ccgcttgcga ggaactactc cggcgcttct cgctggttgc cgatggccgc    900
atcctcacct ccgattacga gtttcatggc gtgcaactga agaaaggtga ccagatcctg    960
ctaccgcaga tgctgtctgg cctggatgag cgcgaaaacg cctgcccgat gcacgtcgac   1020
ttcagtcgcc aaaaggtttc acacaccacc gatggccacg gcagccatct gtgccttggc   1080
cagcacctgg cccgccggga aatcatcgtc accctcaagg aatggctgac caggattcct   1140
gacttctcca ttgccccggg tgcccagatt cagcacaaga gcggcatcgt cagcggcgtg   1200
caggcactcc ctctggtctg ggatccggcg actaccaaag cggtataa               1248
```